(12) United States Patent
Phouybanhdyt et al.

(10) Patent No.: US 7,571,750 B2
(45) Date of Patent: Aug. 11, 2009

(54) TOOL FOR TRANSFERRING CONTROLLED AMOUNTS OF FLUID INTO AND FROM A FLUID FLOW CIRCUIT

(75) Inventors: Hinhsomchay Gnao Phouybanhdyt, Waukesha, WI (US); Edward Emaci, Brookfield, WI (US)

(73) Assignee: General Electric Co., Schenectady, NY (US)

( * ) Notice: Subject to any disclaimer, the term of this patent is extended or adjusted under 35 U.S.C. 154(b) by 666 days.

(21) Appl. No.: 11/161,943

(22) Filed: Aug. 23, 2005

(65) Prior Publication Data

US 2007/0069406 A1   Mar. 29, 2007

(51) Int. Cl.
*B65B 1/04* (2006.01)
*A61M 5/315* (2006.01)

(52) U.S. Cl. .......... 141/321; 141/27; 141/319; 604/236

(58) Field of Classification Search ........ 141/2, 141/18, 27, 319–323, 329; 604/236
See application file for complete search history.

(56) References Cited

U.S. PATENT DOCUMENTS

| | | | |
|---|---|---|---|
| 3,859,985 A * | 1/1975 | Eckhart | 251/344 |
| 4,393,723 A | 7/1983 | Brand | |
| 5,041,087 A * | 8/1991 | Loo et al. | 604/83 |
| 5,240,477 A | 8/1993 | Yamaga et al. | |
| 5,334,163 A * | 8/1994 | Sinnett | 604/236 |
| 5,586,629 A * | 12/1996 | Shoberg et al. | 141/21 |
| 5,957,883 A * | 9/1999 | Lin | 604/36 |
| 6,164,348 A * | 12/2000 | Rodwell et al. | 141/382 |
| 6,360,784 B1 * | 3/2002 | Philippens et al. | 141/2 |
| 6,520,937 B2 | 2/2003 | Hart et al. | |
| 6,676,630 B2 | 1/2004 | Landau et al. | |
| 7,174,923 B2 * | 2/2007 | Schorn et al. | 141/2 |
| 7,398,802 B2 * | 7/2008 | Baker | 141/27 |

* cited by examiner

*Primary Examiner*—Timothy L Maust

(57) ABSTRACT

A tool for transferring controlled amounts of fluid into and from a fluid flow circuit is disclosed herein. The tool includes a substantially closed tube having a first end, a second end, and a chamber therein; an elongate plunger having a fore end extending inside the chamber and toward the second end of the tube, an aft end extending outside the chamber and from the first end of the tube, a piston-like structure on the fore end, and a manipulable structure on the aft end; a fluid inlet duct mounted on the tube; a first coupler mounted on the fluid inlet duct for connecting the duct with the fluid flow circuit; a fluid outlet duct mounted on the second end of the tube; a second coupler mounted on the fluid outlet duct for connecting the duct with the fluid flow circuit; and a fluid transfer duct mounted on the tube.

17 Claims, 25 Drawing Sheets

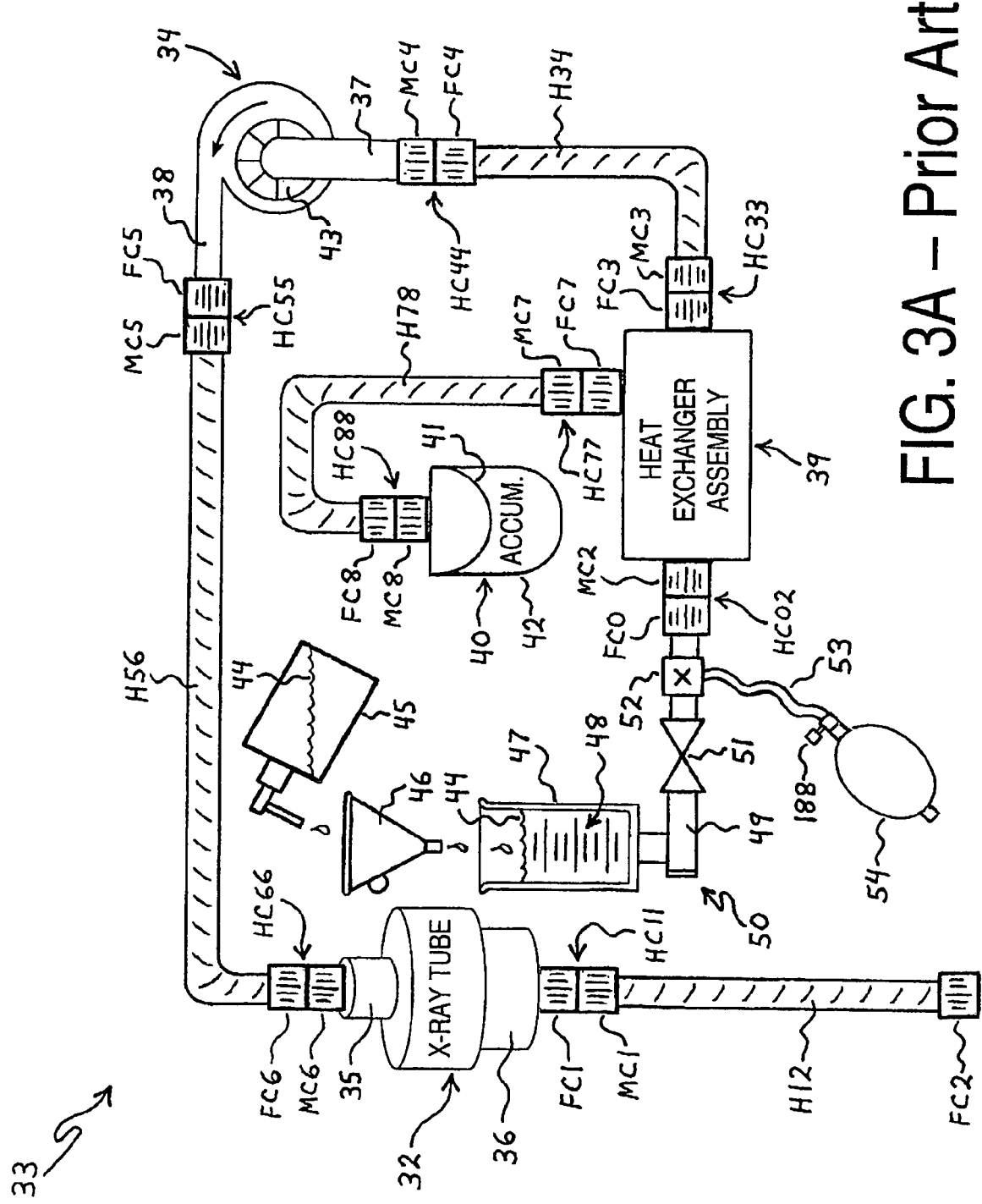
FIG. 3A – Prior Art

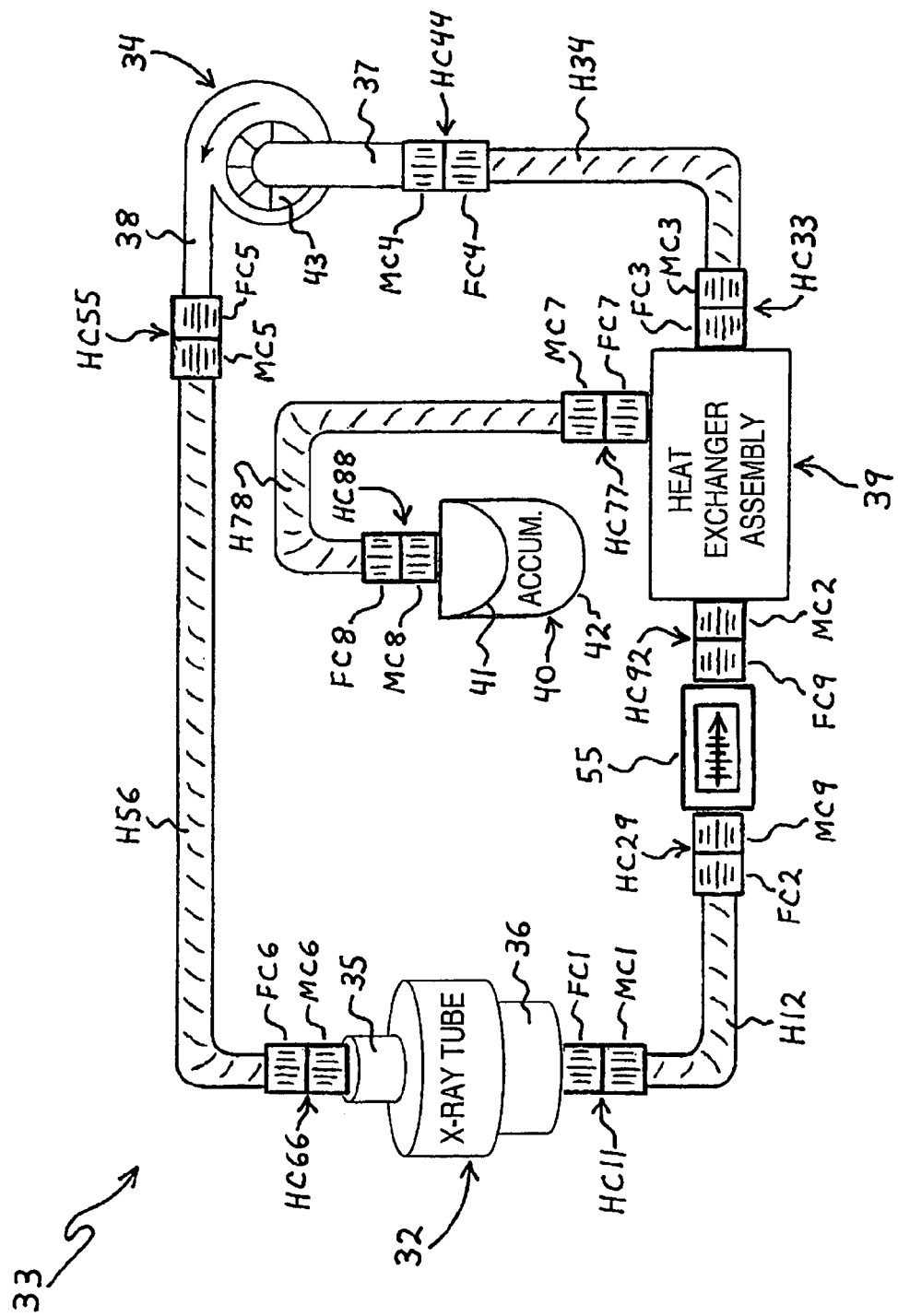
FIG. 3B – Prior Art

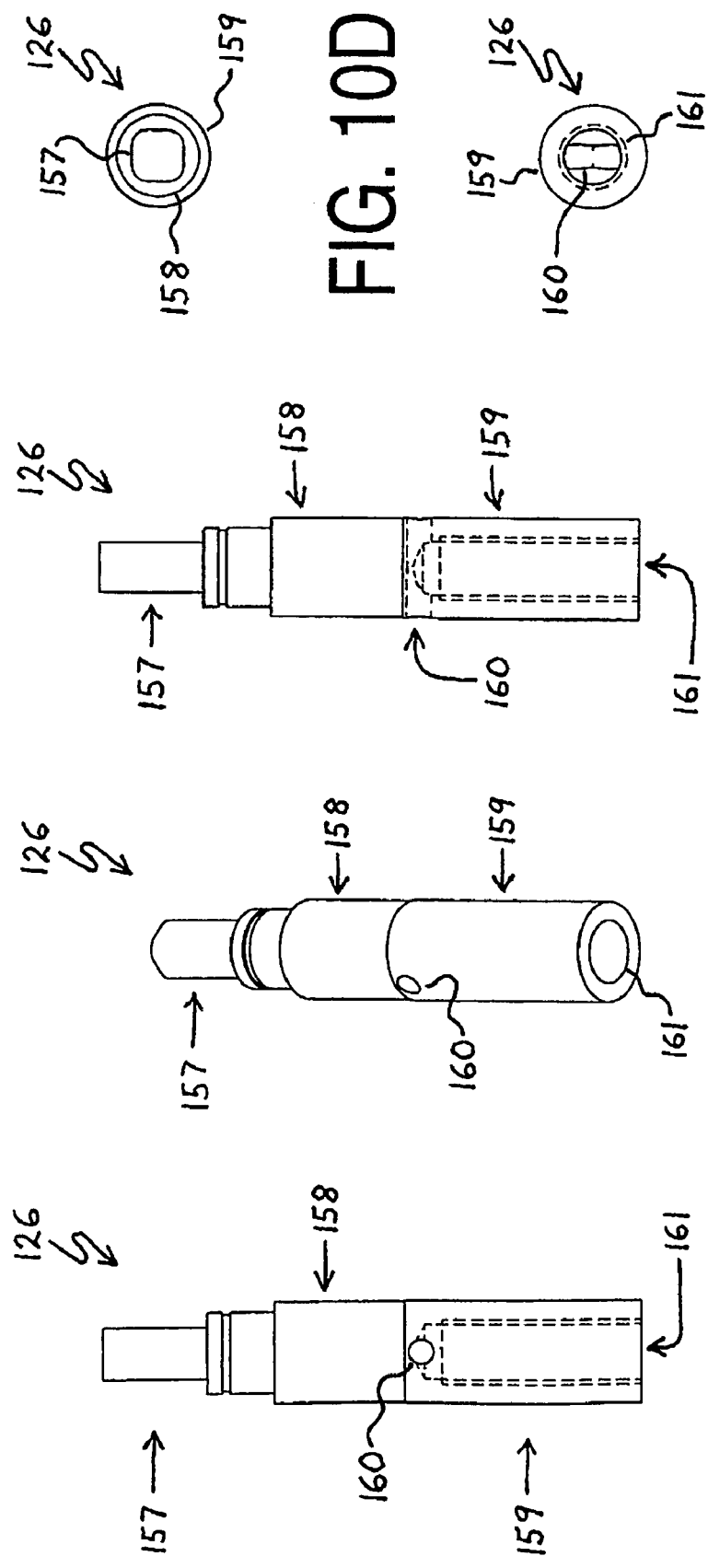

TOOL FOR TRANSFERRING CONTROLLED AMOUNTS OF FLUID INTO AND FROM A FLUID FLOW CIRCUIT

FIELD OF THE INVENTION

The present invention generally relates to fluid flow systems. The present invention more particularly relates to the servicing of various fluid flow circuits and hydraulic systems.

BACKGROUND OF THE INVENTION

In a computed tomography (CT) imaging system or scanner, an x-ray tube is commonly utilized to generate a high-intensity beam of x-rays for irradiating an anatomical region of interest (ROI) within a patient. In utilizing the x-ray tube in this manner, the CT scanner is able to ultimately generate one or more computer images of the patient's ROI for examination and medical diagnosis. During such operation of the CT scanner, the x-ray tube is generally supplied with large amounts of electrical power that are converted into heat, which thereby causes the x-ray tube to get hot. To prevent overheating and burnout of the x-ray tube and any electrical circuitry or mechanical components proximate thereto, a liquid for cooling the x-ray tube is typically passed through the housing in which the x-ray tube is situated. Typically, the liquid is a heat-absorbing "cooling liquid" such as, for example, a dielectric oil.

To systematically pass cooling liquid through the x-ray tube housing, the housing is connected within a fluid flow circuit that circulates the liquid through the housing. The fluid flow circuit, in addition to the x-ray tube housing, usually includes a heat exchanger assembly, a centrifugal pump, and an accumulator. In general, the x-ray tube housing, the heat exchanger assembly, the centrifugal pump, and the accumulator are all interconnected together so as to establish a substantially closed liquid-circulation system with little to no air or gas present therein. The heat exchanger assembly, first of all, generally serves to remove and dissipate heat from the cooling liquid after the liquid has passed through the x-ray tube housing and absorbed heat from the x-ray tube. Once the cooling liquid has been sufficiently cooled by the heat exchanger assembly, the centrifugal pump then serves to pump and re-circulate the cooling liquid back through the x-ray tube housing so as to again draw heat from the x-ray tube. The accumulator, last of all, generally serves to ensure that the cooling liquid is physically accommodated within the fluid flow circuit in a volume-fitted manner and that the overall pressure within the circuit does not significantly increase during expansion of the cooling liquid. The accumulator accomplishes such by elastically adapting to changes in the overall volume of the cooling liquid within the fluid flow circuit, both during volumetric expansion of the liquid when it is hot and during volumetric contraction of the liquid when it is cold. Elastically adapting to volumetric changes in the cooling liquid in this manner is conventionally referred to as "volume compensation" or simply "compensation." To achieve such compensation, the accumulator itself typically includes a sturdy outer housing and an internal membrane protected therein. The internal membrane, in addition to being elastic and expandable, is characteristically impermeable and may comprise, for example, a rubber bladder, diaphragm, or bellows. The maximum supplemental volume provided by such a membrane or bladder when filled with hot liquid and fully expanded is conventionally referred to as its "compensation value."

Per modern convention, the x-ray tube housing, heat exchanger assembly, centrifugal pump, and accumulator are all generally interconnected within the fluid flow circuit by a series of hoses and interlocking couplers. The couplers typically include quick-disconnect (QD) features and internal automatic shut-off valves. Equipped as such, a mating pair of couplers can therefore be easily connected, disconnected, or re-connected by a serviceman in the field without leaking large amounts of cooling liquid from the fluid flow circuit and without introducing large amounts of air into the circuit. In this way, any necessary servicing, maintenance, removal, or replacement of the x-ray tube housing, heat exchanger assembly, centrifugal pump, or accumulator is generally facilitated.

Despite being interconnected in the above-described manner, sometimes a significant amount of cooling liquid is still lost or inadvertently leaked from the fluid flow circuit when servicing one or more of the above-mentioned circuit components. In particular, though the circuit's couplers are typically equipped with automatic shut-off valves, cooling liquid is nevertheless often leaked via one or more of these couplers as they are disconnected and re-connected during service. If such a loss of cooling liquid is not properly corrected, the fluid flow circuit may suffer a corresponding reduction in its overall cooling capability. As a result, overheating and burn-out of the x-ray tube as well as nearby electrical components may occur.

To prevent such potential consequences, a controlled amount of cooling liquid must generally be newly introduced or added into the fluid flow circuit so that the cumulative amount of cooling liquid present within the circuit is restored up to a predetermined proper level. Such a predetermined proper level of cooling liquid is often conventionally referred to as the "compensation level," for the accumulator's bladder in the fluid flow circuit can successfully compensate for (i.e., physically accommodate) any subsequent volumetric expansion of the cooling liquid during operation if the initial cumulative amount of liquid in the circuit does not exceed this predetermined limit level. Thus, when adding cooling liquid to the fluid flow circuit, care must be exercised so as to not add too much liquid and exceed this predetermined limit level, for the expandable bladder of the accumulator may consequently rupture or burst during subsequent operation when the liquid is hot and expanded, thereby potentially causing the spillage of hot oil from the CT scanner. Ultimately, by replenishing the fluid flow circuit with enough cooling liquid so that the cumulative amount of liquid within the circuit is restored back up to compensation level, the circuit's optimum cooling capability is thereby restored and the risk of rupturing the accumulator's bladder is thereby minimized as well. Having to newly introduce or add such a controlled amount of cooling liquid into the fluid flow circuit, however, is often a laborious and undesirably time-consuming task. In particular, according to current convention, a serviceman must generally go through an iterative multi-step fluid insertion and calibration process to ensure the transfer of an appropriate amount of cooling liquid into the fluid flow circuit. Furthermore, since fluid spills while carrying out such a liquid replenishment process are not uncommon, the process is oftentimes rather messy as well.

In addition to sometimes losing cooling liquid, sometimes a significant amount of air is inadvertently introduced into the fluid flow circuit when servicing one or more of the above-mentioned circuit components. In particular, though the circuit's couplers are typically equipped with automatic shut-off valves, air is nevertheless often ingested via one or more of these couplers as they are disconnected and re-connected during service. If such ingestion of air into the fluid flow circuit is not properly corrected, certain consequences may occur. For example, with the introduction of air into the fluid flow circuit, hot pockets of air are apt to develop and be circulated through the circuit during operation, thereby reducing the circuit's overall cooling capability. As a result, highly localized heating and burnout of the x-ray tube as well as nearby electrical components may occur. In addition, artifacts may begin to appear in CT scanner images, thereby reducing scanner image resolution and quality. Furthermore, with air pockets circulating through the fluid flow circuit, the centrifugal pump is likely to begin "choking" and operating less efficiently, and may even incur damage due to cavitation.

To prevent such potential consequences, various different methods have heretofore been proposed for preventing the inadvertent ingestion of air and/or removing air that has already been ingested into a fluid flow circuit. Such methods proposed to date, however, typically involve numerous steps and are characteristically labor intensive. Consequently, the methods are often rather time-consuming and highly inefficient overall. Furthermore, since fluid spills when implementing such methods are not uncommon, the methods are frequently quite messy as well.

In light of the above, there is a present need in the art for a simple tool that is utile for transferring controlled amounts of liquid into and from a fluid flow circuit with minimal spillage and without introducing significant amounts of air into the circuit. For some applications, it is preferable that such a tool also be utile for removing any air or gas bubbles that may already exist in the fluid flow circuit.

SUMMARY OF THE INVENTION

The present invention provides a tool that is generally utile for transferring controlled amounts of fluid into and from a fluid flow circuit. In one practicable embodiment, the tool includes a substantially closed tube, an elongate plunger, a fluid inlet duct, a first coupler, a fluid outlet duct, a second coupler, and a fluid transfer duct. The tube has a first end and a second end, an inner surface and an outer surface, and a chamber defined therein. The plunger has a fore end that extends inside the tube chamber and toward the second end of the tube, and an aft end that extends outside the tube chamber and from the first end of the tube. On the fore end, the plunger includes a piston-like structure that is adapted for establishing and maintaining close sliding contact and a tight seal between the periphery of the piston-like structure and the inner surface of the tube along the length of the tube. On the aft end, the plunger includes a manipulable structure that is adapted for adjusting the position of the piston-like structure within the chamber of the tube. Each of the fluid inlet duct, the fluid outlet duct, and the fluid transfer duct respectively has both a proximal end and a distal end. Regarding the fluid inlet duct, the proximal end of the fluid inlet duct is generally mounted on the tube so as to be in fluid communication with the chamber inside the tube. The distal end of the fluid inlet duct is generally oriented so as to extend away from the tube. For connecting the fluid inlet duct in line with the fluid flow circuit, the first coupler is mounted on the distal end of the fluid inlet duct. Regarding the fluid outlet duct, the proximal end of the fluid outlet duct is particularly mounted on the second end of the tube so as to be in fluid communication with the chamber inside the tube. The distal end of the fluid outlet duct is generally oriented so as to extend away from the tube. For connecting the fluid outlet duct in line with the fluid flow circuit, the second coupler is mounted on the distal end of the fluid outlet duct. Regarding the fluid transfer duct, the proximal end of the fluid transfer duct is generally mounted on the tube so as to be in fluid communication with the chamber inside the tube. The distal end of the fluid transfer duct is generally oriented so as to extend away from the tube.

In addition, the present invention also provides a service tool that is particularly utile for injecting and drawing controlled amounts of liquid into and from a fluid flow circuit with minimal spillage and without introducing significant amounts of air into the circuit. In one practicable embodiment, the service tool includes a substantially closed tube, an elongate plunger, a fluid inlet duct, a first coupler, a fluid outlet duct, a second coupler, and a fluid transfer duct. The tube, in addition to having a first end and a second end, an inner surface and an outer surface, and a chamber defined therein, particularly comprises translucent material and has graduated markings along the length of the tube. In this way, visually determining amounts of fluid, including liquid and any trapped air, within the tube is facilitated. The plunger has a fore end that extends inside the tube chamber and toward the second end of the tube, and an aft end that extends outside the tube chamber and from the first end of the tube. On the fore end, the plunger includes a piston-like structure that is adapted for establishing and maintaining close sliding contact and a tight seal between the periphery of the piston-like structure and the inner surface of the tube along the length of the tube. On the aft end, the plunger includes a manipulable structure that is adapted for adjusting the position of the piston-like structure within the chamber of the tube. Each of the fluid inlet duct, the fluid outlet duct, and the fluid transfer duct respectively has both a proximal end and a distal end. Regarding the fluid inlet duct, the proximal end of the fluid inlet duct is mounted on the tube so as to be in fluid communication with the chamber inside the tube, and the distal end of the fluid inlet duct is oriented so as to extend away from the tube. For connecting the fluid inlet duct in line with the fluid flow circuit, the first coupler is mounted on the distal end of the fluid inlet duct and particularly includes an automatic shut-off valve. The automatic shut-off valve serves to automatically open the fluid inlet duct when connected to the fluid flow circuit and also automatically close the fluid inlet duct when disconnected from the fluid flow circuit. Regarding the fluid outlet duct, the proximal end of the fluid outlet duct is mounted on the second end of the tube so as to be in fluid communication with the chamber inside the tube, and the distal end of the fluid outlet duct is oriented so as to extend away from the tube. For connecting the fluid outlet duct in line with the fluid flow circuit, the second coupler is mounted on the distal end of the fluid outlet duct and particularly includes an automatic shut-off valve. The automatic shut-off valve serves to automatically open the fluid outlet duct when connected to the fluid flow circuit and also automatically close the fluid outlet duct when disconnected from the fluid flow circuit. Regarding the fluid transfer duct, the proximal end of the fluid transfer duct is mounted on the tube so as to be in fluid communication with the chamber inside the tube, and the distal end of the fluid transfer duct is oriented so as to extend away from the tube. The fluid transfer duct particularly includes an adjustable control valve. The adjustable control valve serves to open and close the fluid transfer duct to thereby control amounts of fluid introduced into and removed from the chamber in the tube.

Moreover, the present invention also provides a composite tool. In addition to being utile for transferring controlled amounts of fluid into and from a fluid flow circuit, the composite tool is generally utile for separating out gas bubbles from liquid circulating through the fluid flow circuit and also monitoring the rate of fluid flow through the fluid flow circuit. In one practicable embodiment, the composite tool includes a tool for transferring controlled amounts of fluid into and from the fluid flow circuit, a device for removing gas bubbles from a liquid, and a fluid flow meter. In order to define at least one fluid flow service path through the composite tool, the fluid transfer tool, the gas bubble removal device, and the fluid flow meter are integrated together in an interoperable fashion so as to be in fluid communication with each other.

Furthermore, the present invention also provides a composite service tool. In addition to being utile for injecting and drawing controlled amounts of liquid into and from a fluid flow circuit with minimal spillage and without introducing significant amounts of air into the circuit, the composite service tool is particularly utile for separating out gas bubbles from liquid circulating through the circuit and also monitoring the rate of fluid flow through the circuit. In one practicable embodiment, the composite service tool includes a substantially closed tube, an elongate plunger, a fluid inlet duct, a first coupler, a fluid outlet duct, a second coupler, a fluid transfer duct, a device for removing gas bubbles from a liquid, and a fluid flow meter. The tube comprises translucent material and has a first end and a second end, an inner surface and an outer surface, a chamber defined therein, a fluid inlet port, a fluid outlet port at the second end, and graduated markings along the length of the tube. The plunger has a fore end that extends inside the tube chamber and toward the second end of the tube, and an aft end that extends outside the tube chamber and from the first end of the tube. On the fore end, the plunger includes a piston-like structure that is adapted for establishing and maintaining close sliding contact and a tight seal between the periphery of the piston-like structure and the inner surface of the tube along the length of the tube. On the aft end, the plunger includes a manipulable structure that is adapted for adjusting the position of the piston-like structure within the chamber of the tube. Each of the fluid inlet duct, the fluid outlet duct, and the fluid transfer duct respectively has both a proximal end and a distal end. For connecting the fluid inlet duct in line with the fluid flow circuit, the first coupler is mounted on the distal end of the fluid inlet duct and includes an automatic shut-off valve. For connecting the fluid outlet duct in line with the fluid flow circuit, the second coupler is mounted on the distal end of the fluid outlet duct and includes an automatic shut-off valve. Regarding the fluid transfer duct, the proximal end of the fluid transfer duct is mounted on the tube so as to be in fluid communication with the chamber inside the tube, and the distal end of the fluid transfer duct is oriented so as to extend away from the tube. To control amounts of fluid introduced into and removed from the chamber in the tube, the fluid transfer duct includes an adjustable control valve for opening and closing the fluid transfer duct. Furthermore, in order to define at least one fluid flow service path through the composite service tool, the tube, the gas bubble removal device, and the fluid flow meter are integrated together and connected between the proximal end of the fluid inlet duct and the proximal end of the fluid outlet duct in an interoperable fashion so as to be in fluid communication with each other.

Lastly, it is believed that various other embodiments, design considerations, applications, and advantages of the present invention will become apparent to those skilled in the art when the detailed description of the best mode(s) contemplated for practicing the invention, as set forth hereinbelow, is reviewed in conjunction with the appended claims and the accompanying drawing figures.

BRIEF DESCRIPTION OF THE DRAWINGS

The present invention is described hereinbelow, by way of example, with reference to the following drawing figures.

FIG. 3A is an illustration of a prior art service tool temporarily connected within the fluid flow circuit of FIG. 2 so as to add a certain amount of cooling liquid into the fluid flow circuit.

FIG. 3B is an illustration of a fluid flow meter temporarily connected within the fluid flow circuit of FIG. 2 so as to monitor the flow rate of cooling liquid circulating therein after a certain amount of cooling liquid has been added as shown in FIG. 3A.

FIG. 10A is a front view highlighting the valve body of the composite service tool in FIG. 7B.

FIG. 10B is a perspective bottom view of the valve body in FIG. 10A.

FIG. 10C is a side view of the valve body in FIG. 10A.

FIG. 10D is a top view of the valve body in FIG. 10A.

FIG. 10E is a bottom view of the valve body in FIG. 10A.

DETAILED DESCRIPTION OF THE INVENTION

Figure 1:
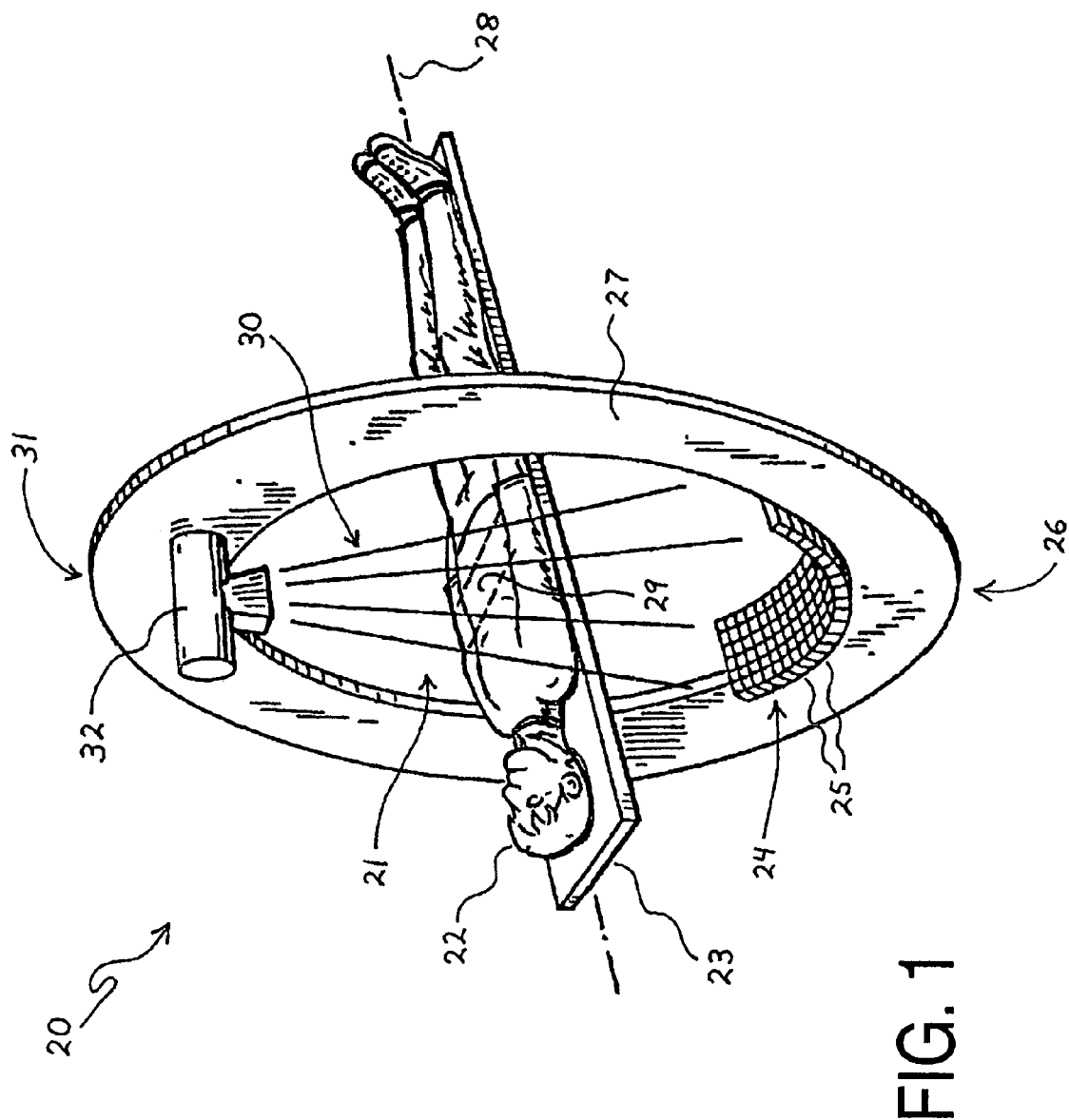
FIG. 1 is a perspective view highlighting some of the primary scanning elements in a largely conventional computed tomography (CT) imaging system.

FIG. 1 is a perspective view highlighting some of the primary scanning elements in a largely conventional computed tomography (CT) imaging system 20. As shown, the CT imaging system 20 includes an elongated patient table 23, an annular gantry 27, an x-ray tube 32, and an arcuate detector 24. In general, the patient table 23 is situated within an aperture or opening 21 defined within the gantry 27 so as to be collinearly aligned with an axis 28 defined through the center of the gantry's opening 21. The x-ray tube 32 is mounted at or near a 12 o'clock position 31 on the gantry 27, and the detector 24 is mounted at or near a 6 o'clock position 26 on the gantry 27.

For operation of the CT imaging system 20, a subject or patient 22 is laid upon the patient table 23, and the table 23 is moved along the gantry axis 28 by an electric motor (not shown) so as to position a particular anatomical section or region of interest (ROI) 29 within the patient 22 underneath the x-ray tube 32. Once the patient 22 is aligned underneath the x-ray tube 32 as desired, movement of the patient table 23 is then arrested so as to immobilize both the table 23 and the patient 22. After the table 23 and patient 22 are immobilized, the gantry 27 is activated and thereby proceeds to rotate or spin about the patient 22 lying on the table 23. As the gantry 27 spins, the x-ray tube 32 emits a fan-shaped beam of x-rays 30 toward the patient 22. In this way, the patient's ROI 29 is thoroughly irradiated with x-rays 30 from many different angles. As the x-rays 30 attempt to pass through the patient 22 during such irradiation, the x-rays 30 are individually absorbed or attenuated (i.e., weakened) at various differing levels depending on the particular biological tissues existing within the ROI 29. These differing levels of x-ray absorption or attenuation are sensed and detected by an array of x-ray detector elements 25 included within the detector 24 and situated opposite the x-ray tube 32. Based on these differing levels as detected, the CT imaging system 20 is able to generate x-ray strength profiles and therefrom "construct" digital images of the patient's ROI 29 with the help of data-processing computers (not shown). Upon constructing such images, the images may be visibly displayed on a computer monitor (not shown) so that a doctor or other medical professional can indirectly observe and examine the ROI 29 within the patient 22. After conducting such an examination, the doctor can then accurately diagnose a patient's malady and prescribe an appropriate treatment.

During such operation of the conventional CT imaging system 20 depicted in FIG. 1, the x-ray tube 32 is supplied with large amounts of electrical power and, therefore, tends to get hot. To prevent overheating and burnout of the x-ray tube 32 and any electrical circuitry or components proximate thereto, a liquid for cooling the x-ray tube 32 is passed through the housing in which the x-ray tube 32 is situated. According to convention, the liquid is typically a heat-absorbing type of liquid such as, for example, a dielectric oil. To systematically pass the cooling liquid through the housing of the x-ray tube 32, the x-ray tube 32 is connected within a fluid flow circuit that circulates the liquid through the housing.

Figure 2:
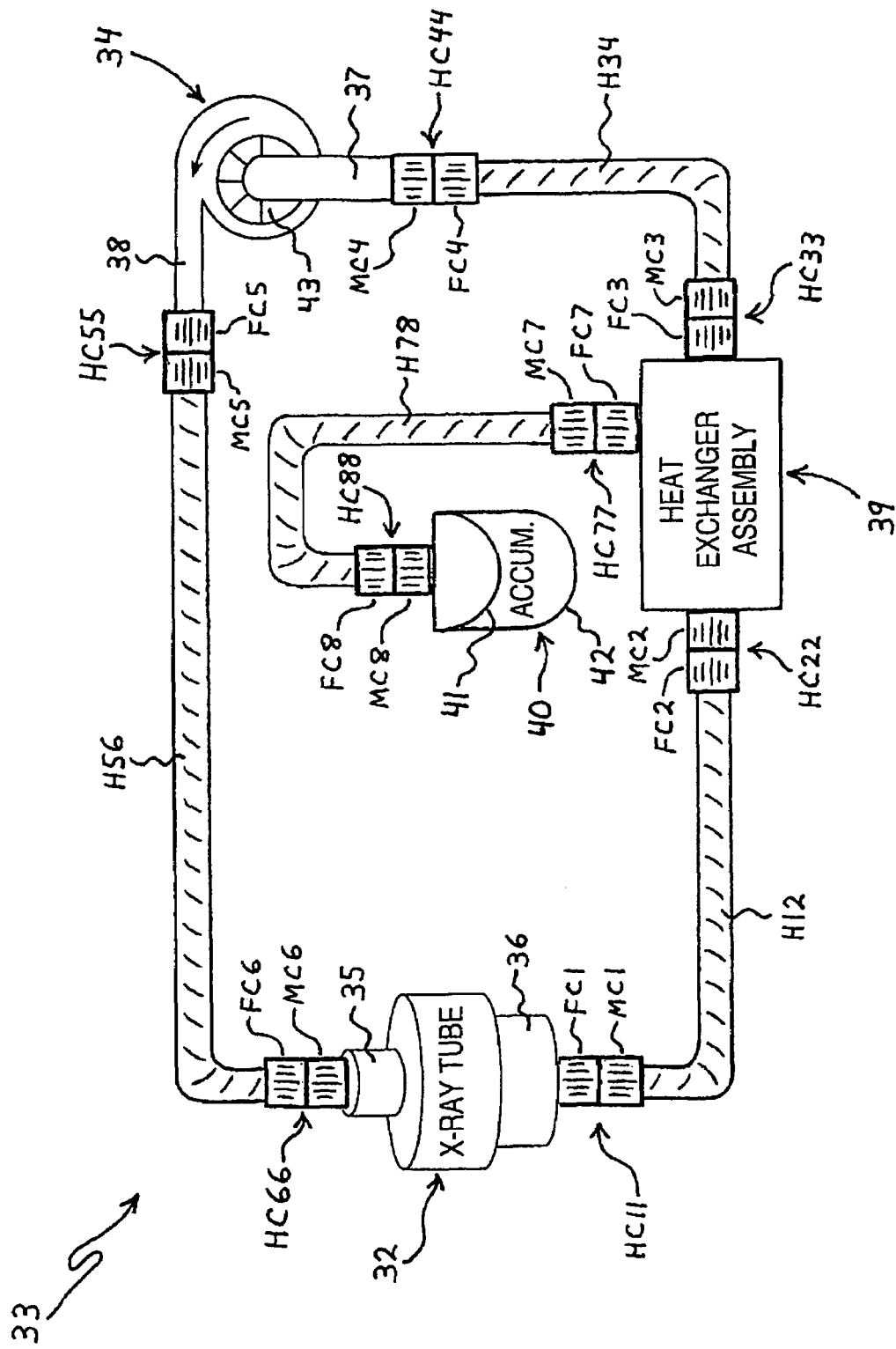
FIG. 2 is an illustration of a largely conventional fluid flow circuit for an x-ray tube cooling system suitable for use in the CT imaging system of FIG. 1.

FIG. 2 is an illustration of a largely conventional fluid flow circuit 33 for an x-ray tube cooling system that is suitable for use in the CT imaging system 20 of FIG. 1. As shown in FIG. 2, the fluid flow circuit 33, in addition to the x-ray tube 32, includes a heat exchanger assembly 39, a centrifugal pump 34, and an accumulator 40. In general, the x-ray tube 32, the heat exchanger assembly 39, the centrifugal pump 34, and the accumulator 40 are all interconnected together so as to establish a substantially closed liquid-circulation system with little to no air or gas present therein. The heat exchanger assembly 39, first of all, generally serves to remove and dissipate heat from the cooling liquid after the liquid has passed through the x-ray tube housing and absorbed heat from the x-ray tube 32. Once the cooling liquid has been sufficiently cooled by the heat exchanger assembly 39, the centrifugal pump 34 then serves to pump and re-circulate the cooling liquid back through the x-ray tube housing so as to again draw heat from the x-ray tube 32. The accumulator 40, last of all, generally serves to ensure that the cooling liquid is physically accommodated within the fluid flow circuit 33 in a volume-fitted manner. The accumulator 40 accomplishes such by elastically adapting to changes in the overall volume of the cooling liquid within the fluid flow circuit 33, both during volumetric expansion of the liquid when it is hot and during volumetric contraction of the liquid when it is cold. The accumulator 40 itself includes a sturdy outer housing 42 and an internal membrane 41 protected therein. The internal membrane 41, in addition to being elastic and expandable, is characteristically impermeable and may comprise, for example, a rubber bladder, diaphragm, or bellows. Within such a configuration, the internal membrane 41 is able to freely expand into the recess of the accumulator's housing 42 whenever the cooling liquid in the fluid flow circuit 33 is particularly hot.

As further shown in FIG. 2, the x-ray tube 32, the heat exchanger assembly 39, the centrifugal pump 34, and the accumulator 40 are all generally interconnected within the fluid flow circuit 33 by a series of hoses H12, H34, H56, and H78. Each hose respectively has a male coupler (MC) affixed on one end and a female coupler (FC) affixed on its other end. With each hose individually constructed as such, a hydraulic coupling (HC) is successfully formed when the male or female coupler of a hose is properly "mated" (i.e., releasibly interlocked) with a female or male coupler associated with one of the circuit's components. Preferably, the male and female couplers themselves include quick-disconnect (QD) features and internal automatic shut-off valves. Equipped as such, a mating pair of couplers can therefore be easily connected, disconnected, or re-connected by a serviceman in the field without leaking large amounts of cooling liquid from the fluid flow circuit 33 and without introducing large amounts of air into the circuit 33. In this way, any necessary servicing, maintenance, removal, or replacement of the x-ray tube 32, heat exchanger assembly 39, centrifugal pump 34, or accumulator 40 is generally facilitated.

Despite being interconnected in the above-described manner, sometimes a significant amount of cooling liquid is still lost or inadvertently leaked from the fluid flow circuit 33 when servicing one or more of the above-mentioned circuit components. In particular, though the circuit's couplers are equipped with automatic shut-off valves, cooling liquid is nevertheless often leaked via one or more of these couplers as they are disconnected and re-connected during service. If such a loss of cooling liquid is not properly corrected, the fluid flow circuit 33 may suffer a corresponding reduction in its overall cooling capability. As a result, overheating and burnout of the x-ray tube 32 as well as nearby electrical components may occur.

To prevent such potential consequences, a controlled amount of cooling liquid must generally be newly introduced or added into the fluid flow circuit 33 so that the cumulative amount of cooling liquid present within the circuit 33 is restored up to a predetermined proper level. As alluded to hereinabove, such a predetermined proper level of cooling liquid in the fluid flow circuit 33 is often conventionally referred to as the "compensation level." In general, as long as the cumulative amount of cooling liquid in the fluid flow circuit 33 is maintained so as to not exceed this predetermined limit level, the accumulator's bladder in the circuit 33 can successfully compensate for (i.e., physically accommodate) any volumetric expansion of the cooling liquid during operation. Thus, when adding cooling liquid to the fluid flow circuit 33, care must be exercised so as to not add too much liquid and exceed this predetermined limit level, for the expandable bladder of the accumulator 40 may consequently rupture or burst during subsequent operation when the liquid is hot and expanded, thereby potentially causing the spillage of hot oil from the CT imaging system 20. Ultimately, by replenishing the fluid flow circuit 33 with enough cooling liquid so that the cumulative amount of liquid within the circuit 33 is restored back up to compensation level, the circuit's optimum cooling capability is thereby restored and the risk of rupturing the accumulator's bladder is thereby minimized as well.

For adding a controlled amount of cooling liquid into the fluid flow circuit 33 so as to properly restore the cumulative amount of liquid in the circuit 33 back up to compensation level, various prior art service tools have heretofore been utilized by servicemen in the field. FIG. 3A illustrates one such prior art service tool 50 as a representative example. As depicted, the prior art service tool 50 basically includes an open-top transparent cylinder 47, piping 49, a backflow prevention valve 51, an air jack 52, an air hose 53, a hand-squeezable inflation bulb 54, an air release button 188, and a female coupler FC0. The transparent cylinder 47, first of all, has graduated markings 48 along its length and also a hole defined in its bottom. The bottom of the graduated cylinder 47 is affixed to the first end of the piping 49 so that fluid communication is established with the piping's inner hollow via the cylinder's bottom hole. The piping 49, in turn, has both the backflow prevention valve 51 and the air jack 52 operatively incorporated along its length and also the female coupler FC0 affixed to its second end. The inflation bulb 54 along with its associated air release button 188, lastly, is operatively connected to the air jack 52 by means of the air hose 53. In this way, fluid communication between the inflation bulb 54 and the piping 49 is established as well.

To use the prior art service tool 50, the female coupler FC2 and the male coupler MC2 of the fluid flow circuit 33 must first be disconnected from each other. Because each of the couplers FC2 and MC2 has its own automatic shut-off valve (not shown) incorporated therein, cooling liquid already present and remaining within the fluid flow circuit 33 is prevented from freely flowing out of the circuit 33 when the couplers FC2 and MC2 are disconnected. Once the couplers FC2 and MC2 are disconnected and separated from each other, the prior art service tool 50 is then temporarily connected within the fluid flow circuit 33 by means of the coupler FC0 as shown in FIG. 3A. Upon being connected within the fluid flow circuit 33 as such, the prior art service tool 50 is then able to receive cooling liquid 44, dispensed from a bottle 45 and passed through a funnel 46, via the open top of its graduated cylinder 47. Once the cooling liquid 44 is received in the cylinder 47, the liquid 44 is then drawn through the backflow prevention valve 51 and into the fluid flow circuit 33 by creating a vacuum within the circuit 33 through manipulation of the inflation bulb 54 and its associated air release button 188. By visually observing the amount(s) of cooling liquid 44 introduced into the cylinder 47, visually referencing the graduated markings 48 along the cylinder's length, and visually monitoring the accumulator bladder's degree of expansion, increments of cooling liquid 44 can thus be added to the fluid flow circuit 33 in a largely controlled manner. In this way, an appropriate amount of cooling liquid 44 is ultimately added to the fluid flow circuit 33 so as to properly restore the cumulative amount of liquid 44 in the circuit 33 back up to compensation level. Once the cumulative amount of cooling liquid 44 in the fluid flow circuit 33 is successfully replenished to compensation level in this manner, the prior art service tool 50 is disconnected and removed from the circuit 33. After the service tool 50 is removed, a fluid flow meter 55 is then temporarily connected within the fluid flow circuit 33 in a closed-loop fashion as shown in FIG. 3B. Once the fluid flow meter 55 is connected within the fluid flow circuit 33, the centrifugal pump 34 is activated so as to circulate the cooling liquid 44 throughout the circuit 33. By circulating the cooling liquid 44 through the fluid flow circuit 33 in this way just after an amount of liquid 44 has been added as described hereinabove, the overall flow rate of the cumulative liquid 44 circulating through the circuit 33 can be preliminarily tested and carefully monitored so as to ensure that the x-ray tube 32 will be properly cooled during subsequent actual operation of the CT imaging system 20. If the overall flow rate as indicated by the fluid flow meter 55 is within a predetermined proper operating range, the centrifugal pump 34 is turned off and the fluid flow meter 55 is disconnected and removed from the fluid flow circuit 33. Once the fluid flow meter 55 is removed, the couplers FC2 and MC2 are then reconnected together as originally shown in FIG. 2. After the couplers FC2 and MC2 are reconnected, the centrifugal pump 34 may then be reactivated as desired for full operation of the CT imaging system 20.

As FIGS. 3A and 3B suggest, however, having to newly introduce or add a controlled amount of cooling liquid 44 into the fluid flow circuit 33 by means of such a prior art service tool 50 is often a laborious and undesirably time-consuming task. In particular, a serviceman must generally go through an iterative multi-step calibration process wherein cooling liquid 44 is slowly introduced into the fluid flow circuit 33 in controlled increments so as to ultimately ensure the transfer of an appropriate amount of liquid 44 into the circuit 33. Furthermore, since adding cooling liquid 44 into the fluid flow circuit 33 by means of the prior art service tool 50 involves use of an open-top cylinder 47 that is in open communication with ambient air, air bubbles are sometimes inadvertently introduced into the circuit 33 and unintended fluid spills occasionally take place as well. Fluid spills, in particular, are especially apt to occur if the fluid flow circuit 33 is mounted at or near the 12 o'clock position 31 on the CT imaging system's gantry 27, for a serviceman must oftentimes stand on a stepladder and lean over the system 20 so as to connect the service tool 50 into the circuit 33 and pour cooling liquid 44 into the tool's open-top cylinder 47. In light of these drawbacks associated with using such a prior art service tool 50, there is now a clear and present need in the art for a new service tool that is utile for transferring controlled amounts of liquid into a fluid flow circuit with minimal spillage and without introducing significant amounts of air into the circuit.

Furthermore, at times when the x-ray tube 32 is temporarily disconnected and removed from the fluid flow circuit 33 so as to service or replace a malfunctioning component in the tube 32, the tube 32 is sometimes particularly removed while it is still hot from operation. In this way, after the x-ray tube 32 is drained of cooling liquid, the tube 32 can be serviced in an expedited manner so as to minimize downtime (i.e., unavailability) of the CT imaging system 20. After being properly serviced, the x-ray tube 32 itself is generally topped off (i.e., filled) with cooling liquid before being reconnected within the fluid flow circuit 33. Because the x-ray tube 32 is disconnected from the circuit 33 while still hot, however, an excess amount of cooling liquid is generally retained within the expanded bladder of the accumulator 40 as the tube 32 is serviced. Hence, if the x-ray tube 32 is disconnected (while hot), serviced, and reconnected in this manner multiple times, the cumulative amount of cooling liquid within the fluid flow circuit 33 may inadvertently increase over time and ultimately come to significantly exceed proper compensation level. If such occurs, the accumulator's bladder may not be able to successfully compensate for (i.e., physically accommodate) the cooling liquid, especially during volumetric expansion of the cooling liquid when absorbing heat from the x-ray tube 32 during operation of the CT imaging system 20. Consequently, the accumulator's bladder may rupture or burst. To prevent such from occurring, sometimes a controlled amount of cooling liquid must therefore be drawn and removed from the fluid flow circuit 33 to ensure that proper compensation level is not exceeded. As briefly described hereinabove, however, the prior art service tool 50 is generally only utile for adding controlled amounts of liquid into a fluid flow circuit and is generally not utile for removing controlled amounts of liquid from a circuit. In light of this drawback associated with using such a prior art service tool 50, there is now also a clear and present need in the art for a new service tool that is utile for drawing and removing controlled amounts of liquid from a fluid flow circuit.

FIGS. 4A through 5D co-illustrate a newly proposed service tool 60 that is generally utile for transferring controlled amounts of fluid both into and from a fluid flow circuit. This service tool 60, as depicted, is a first practicable embodiment of the present invention. As best illustrated in FIGS. 5A through 5D, the service tool 60 itself includes a substantially closed tube 65, an elongate plunger 70, a fluid inlet duct 63, a first coupler MC10, a fluid outlet duct 64, a second coupler FC10, and a fluid transfer duct 61. The tube 65 has a first end 71 and a second end 72, an inner surface 74 and an outer surface 75, and a chamber 80 defined therein. The plunger 70 has a fore end 69 that extends inside the tube chamber 80 and toward the second end 72 of the tube 65, and an aft end 73 that extends outside the tube chamber 80 and from the first end 71 of the tube 65. On the fore end 69, the plunger 70 includes a piston-like structure 90 that is adapted for establishing and maintaining close sliding contact and a tight seal between the periphery of the piston-like structure 90 and the inner surface 74 of the tube 65 along the length of the tube 65. On the aft end 73, the plunger 70 includes a manipulable structure 68 that is adapted for adjusting the position of the piston-like structure 90 within the chamber 80 of the tube 65. Each of the fluid inlet duct 63, the fluid outlet duct 64, and the fluid transfer duct 61 respectively has both a proximal end and a distal end. Regarding the fluid inlet duct 63, the proximal end 82 of the fluid inlet duct 63 is generally mounted on the tube 65 so as to be in fluid communication with the chamber 80 inside the tube 65. The distal end 83 of the fluid inlet duct 63 is generally oriented so as to extend away from the tube 65. For connecting the fluid inlet duct 63 in line with the fluid flow circuit 33, the first coupler MC10 is mounted on the distal end 83 of the fluid inlet duct 63. Regarding the fluid outlet duct 64, the proximal end 84 of the fluid outlet duct 64 is particularly mounted on the second end 72 of the tube 65 so as to be in fluid communication with the chamber 80 inside the tube 65. The distal end 85 of the fluid outlet duct 64 is generally oriented so as to extend away from the tube 65. For connecting the fluid outlet duct 64 in line with the fluid flow circuit 33, the second coupler FC10 is mounted on the distal end 85 of the fluid outlet duct 64. Regarding the fluid transfer duct 61, the proximal end 91 of the fluid transfer duct 61 is generally mounted on the tube 65 so as to be in fluid communication with the chamber 80 inside the tube 65. The distal end 92 of the fluid transfer duct 61 is generally oriented so as to extend away from the tube 65.

Figure 4A:
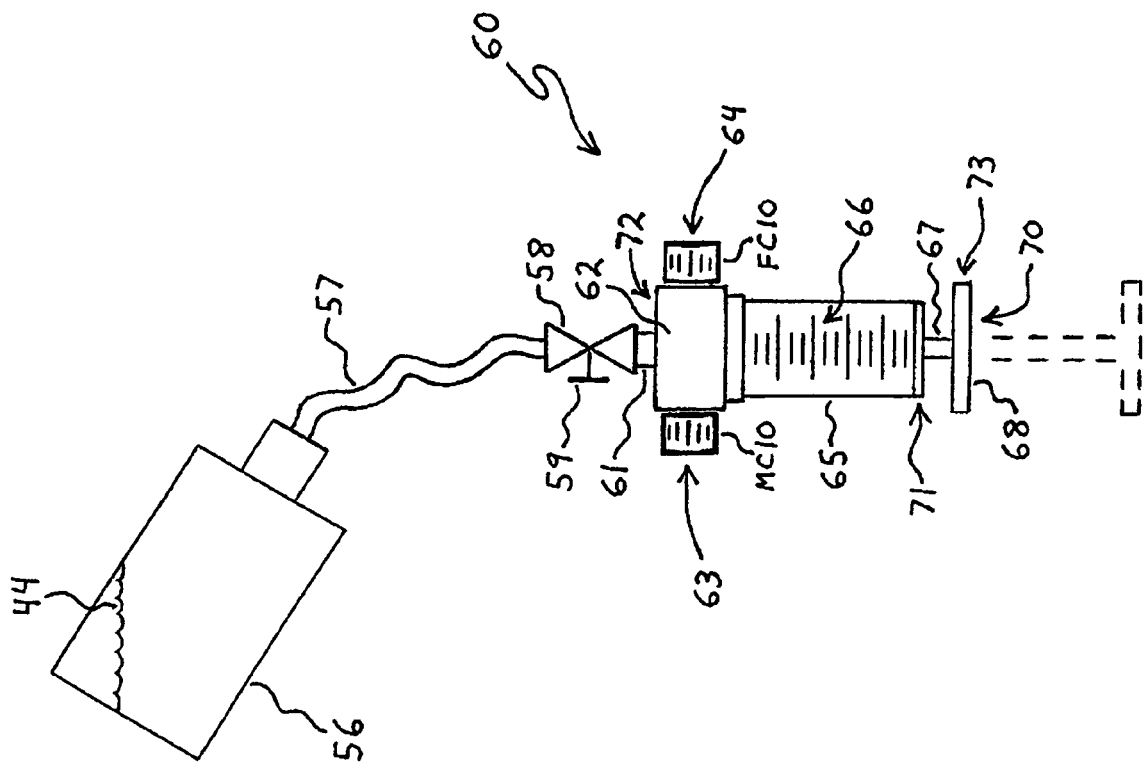
FIG. 4A is an illustration of cooling liquid being introduced into a service tool. The service tool in FIG. 4A is a first practicable embodiment of the invention disclosed herein.
Figure 5A:
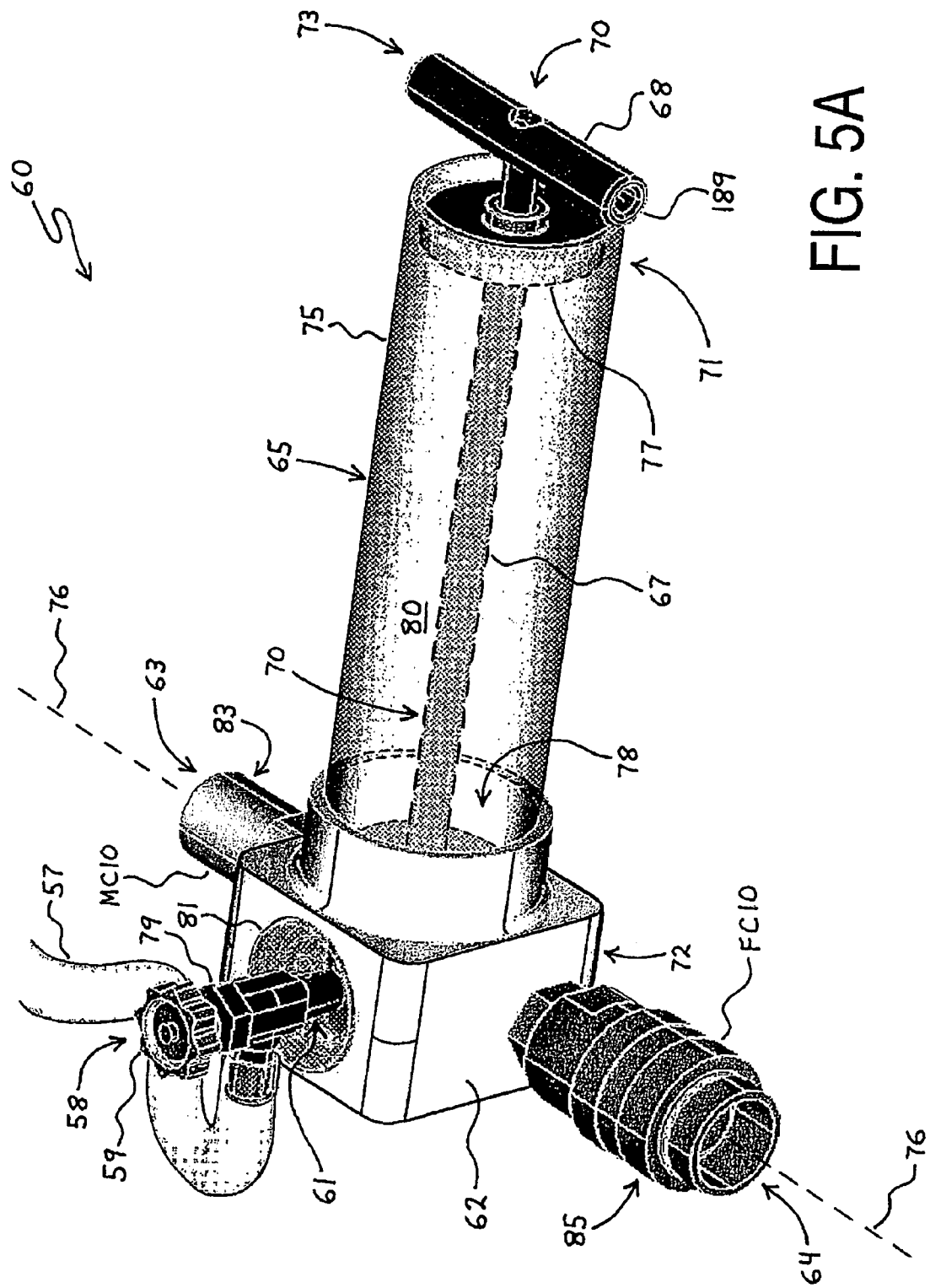
FIG. 5A is a perspective side-to-front view of the service tool in FIG. 4A.

As shown in FIG. 5A, the tube 65 of the service tool 60 preferably has a circular cross section and thus a substantially cylindrical shape overall. In alternative embodiments, however, the tube 65 may instead have a cross section that is, for example, oval, elliptical, polygonal, et cetera. In addition, the tube 65 is preferably formed from a clear, transparent, or translucent material such as shatterproof plastic (polycarbonate). In alternative embodiments, however, the tube 65 may instead be formed from other transparent or translucent materials such as, for example, glass or the like. Composed of such, the tube 65 is characteristically see-through. As a result, a serviceman is generally able to visually determine both the presence and amount of any one or more fluids (for example, air, liquid, etc.) within the tube 65. Furthermore, as shown in FIG. 4A, the tube 65 preferably has graduated markings 66 along its length. In having such markings 66, the tube 65 facilitates a serviceman's being able to visually determine amounts of fluid within the tube 65 with more precision.

In addition to including the piston-like structure 90 and the manipulable structure 68, the elongate plunger 70 also includes a shaft 67. As co-illustrated in FIGS. 5A and 5C, the shaft 67 joins the piston-like structure 90 and the manipulable structure 68 together. To accommodate the shaft 67, the first end 71 of the tube 65 has a fixed end cap 77 with a hole defined therethrough so as to permit back-and-forth movement of the shaft 67 through the hole. Within this configuration, the manipulable structure 68 is preferably shaped as a handle for thereby enabling a serviceman to manually push and pull the plunger 70 into various longitudinal positions as desired. The piston-like structure 90, in turn, preferably comprises a piston disc with a peripheral or circumferential groove 93 for closely receiving and retaining an o-ring. Retained as such, the o-ring (not shown) serves to help establish and maintain both close sliding contact and a tight seal between the periphery of the piston-like structure 90 and the inner surface 74 of the tube 65 during movement of the structure 90 within and along the length of the tube 65. The o-ring itself is preferably made of an elastic or resilient material that is particularly compatible with the type of cooling liquid being circulated in the fluid flow circuit 33. In some embodiments, such an elastic or resilient material may be, for example, rubber.

Figure 5B:
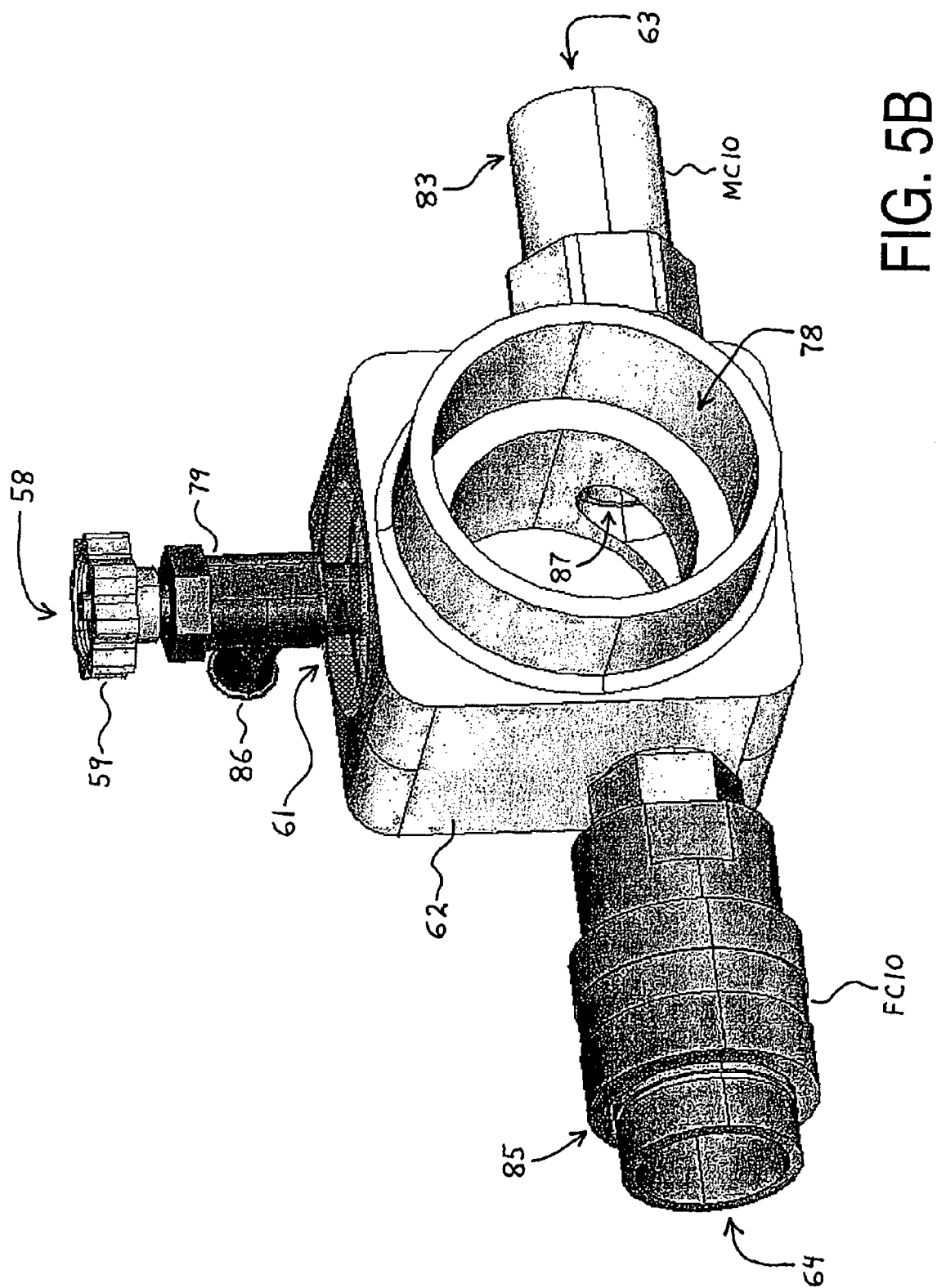
FIG. 5B is a perspective side-to-front view highlighting the machined end block mount of the service tool in FIG. 5A.
Figure 5C:
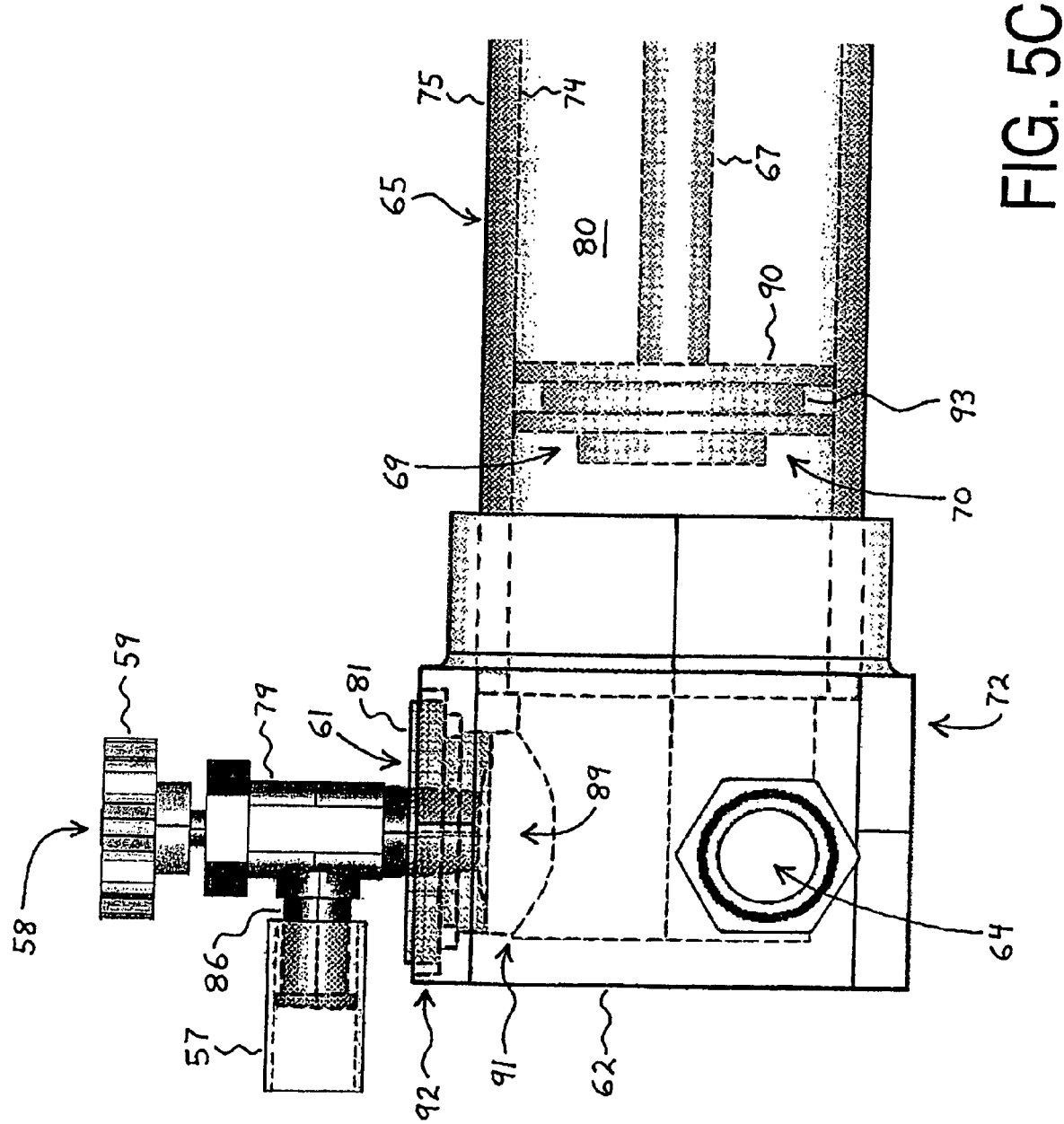
FIG. 5C is a side view highlighting both the machined end block mount and the elongate plunger of the service tool in FIG. 5A.
Figure 5D:
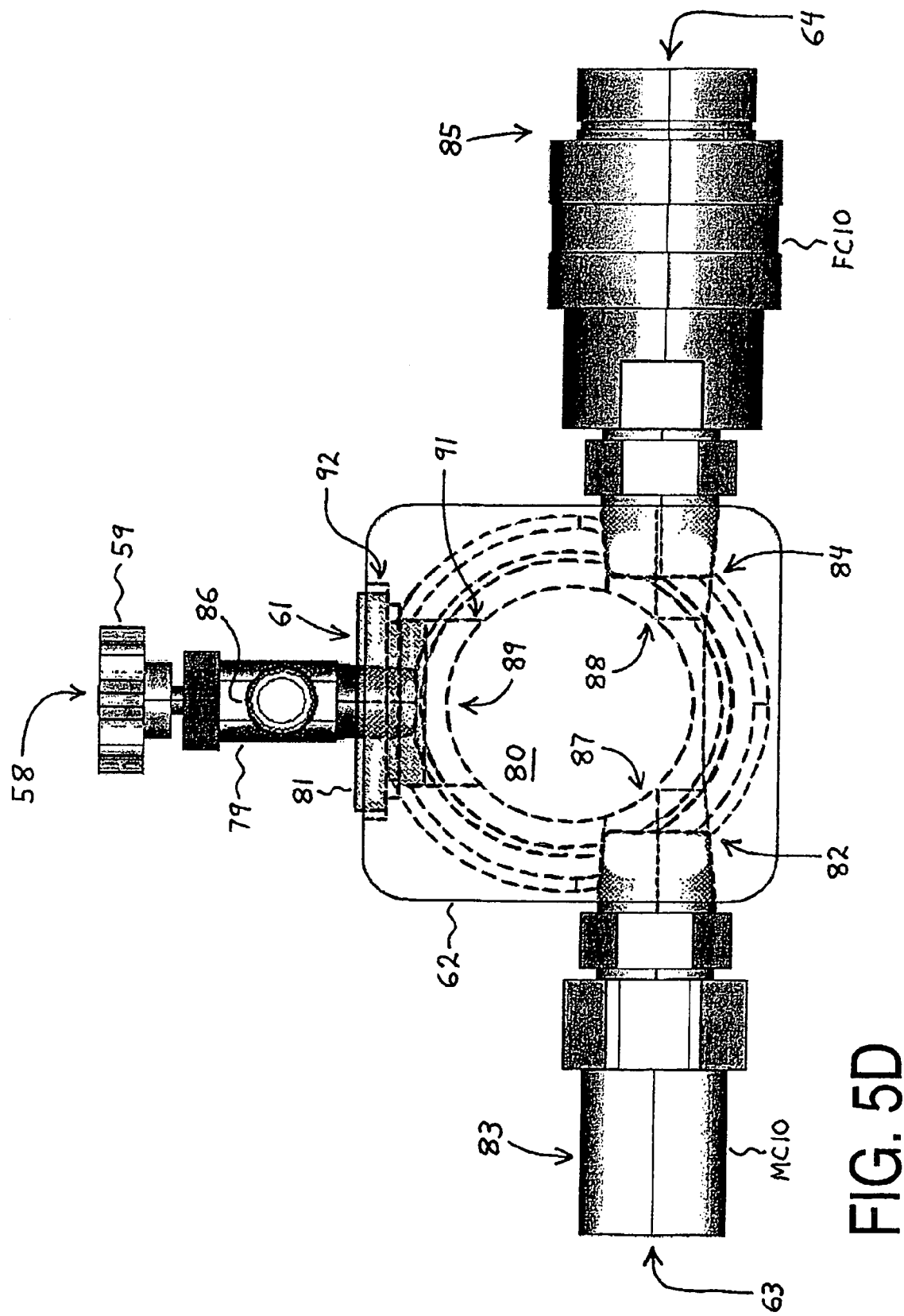
FIG. 5D is a rear view highlighting both the machined end block mount and the couplers of the service tool in FIG. 5A.

As best shown in FIGS. 5A and 5D, the proximal end 84 of the fluid outlet duct 64 is preferably mounted at or near the second end 72 of the tube 65. Mounted as such, the fluid outlet duct 64 is thereby able to expel the fluid contents of the tube 65 whenever the piston-like structure 90 of the plunger 70 is pushed to the second end 72 of the tube 65. Though also shown mounted at the second end 72 of the tube 65, both the proximal end 82 of the fluid inlet duct 63 and the proximal end 91 of the fluid transfer duct 61 may, in alternative embodiments, be individually mounted at various other points along the length of the tube 65, even proximate the first end 71 of the tube 65. In addition, though shown mounted on the tube 65 separate from both the fluid inlet duct 63 and the fluid outlet duct 64, the proximal end 91 of the fluid transfer duct 61 may, in other alternative embodiments, be physically conjoined or coextensive with either the proximal end 82 of the fluid inlet duct 63 or the proximal end 84 of the fluid outlet duct 64. Furthermore, in still other alternative embodiments, the physically distinct fluid transfer duct 61 may be eliminated altogether so that only the fluid inlet duct 63 and the fluid outlet duct 64 remain mounted on the tube 65. In such embodiments sans a physically distinct fluid transfer duct, either or both of the fluid inlet duct 63 and the fluid outlet duct 64 may additionally serve as a fluid transfer duct for filling and/or emptying the tube 65.

Figure 4B:
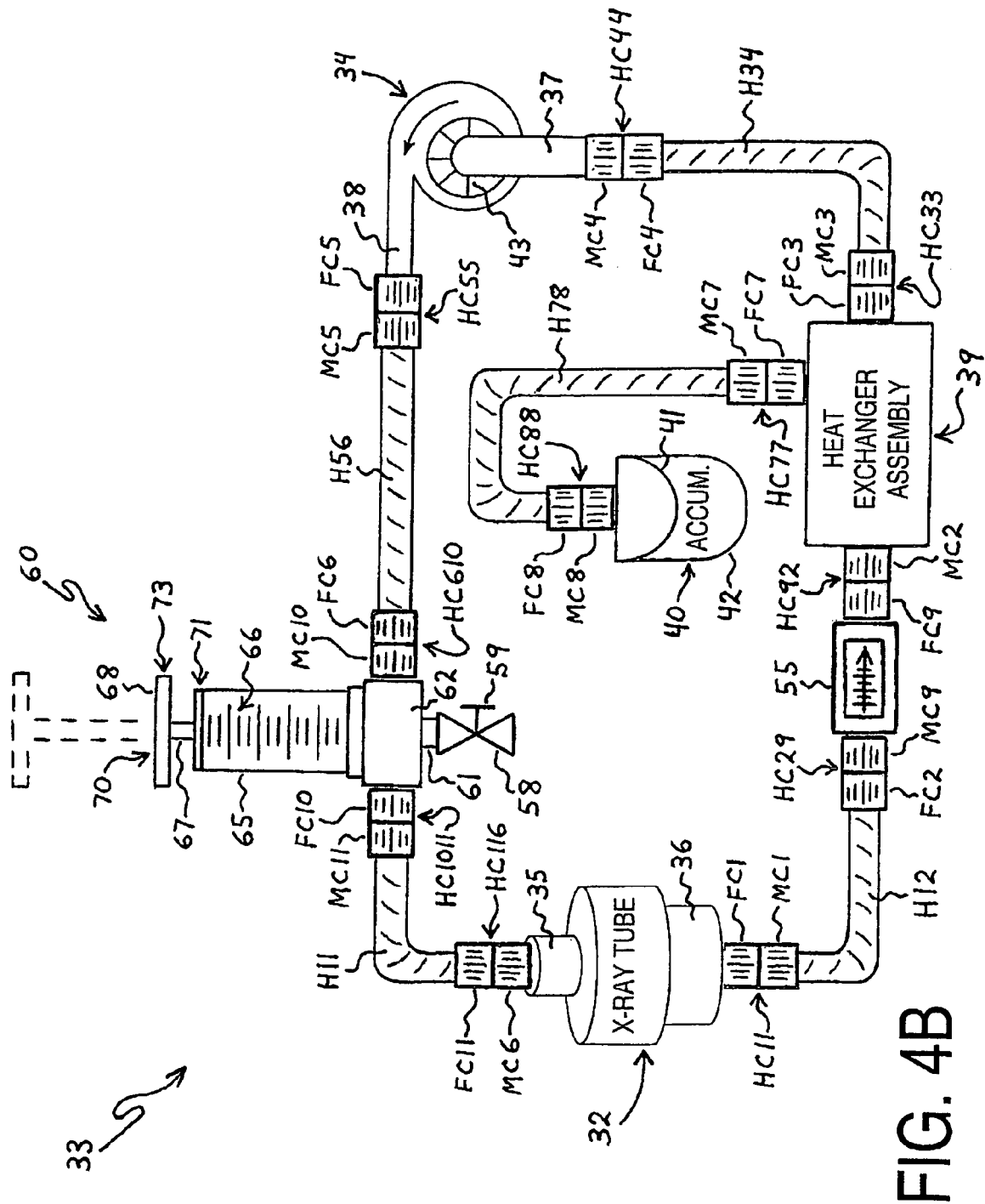
FIG. 4B is an illustration of the service tool in FIG. 4A and a fluid flow meter both temporarily connected within the fluid flow circuit of FIG. 2. Connected as such, the service tool is operable to transfer a controlled amount of cooling liquid into the fluid flow circuit, and the fluid flow meter is operable to monitor the flow rate of cooling liquid circulating therein.

As illustrated in FIGS. 5A, 5B, and 5D, the distal end 83 of the fluid inlet duct 63 and the distal end 85 of the fluid outlet duct 64 are preferably arranged so as to face in substantially opposite directions. In this way, a serviceman is better able to connect the service tool 60 in line with a fluid flow circuit, such as shown in FIG. 4B. Most preferably, however, the distal end 83 of the fluid inlet duct 63 and the distal end 85 of the fluid outlet duct 64 are particularly arranged so as to be axially aligned with each other, as is shown in FIG. 5A with respect to duct alignment axis 76. In this way, a serviceman is even better able to connect the service tool 60 in line with a fluid flow circuit.

As configured on the service tool 60, the first coupler MC10 is a male type coupler that is adapted for receipt within a female coupler associated with a fluid flow circuit. The second coupler FC10, on the other hand, is a female type coupler that is adapted for receiving a fluid flow circuit's male coupler. As is preferred, both the first coupler MC10 and the second coupler FC10 respectively include quick-disconnect (QD) features. Equipped as such, both the first coupler MC10 and the second coupler FC10 can thus be connected to and disconnected from the couplers of a fluid flow circuit in a quick and easy fashion. As is also preferred, both the first coupler MC10 and the second coupler FC10 respectively include internal automatic shut-off valves (not particularly shown). In general, each shut-off valve is adapted so as to automatically permit an open flow of fluid through its associated coupler whenever the coupler is properly mated with another coupler. In addition, each shut-off valve is also adapted so as to automatically shut off the flow of fluid through its associated coupler whenever the coupler is disconnected from another coupler. Equipped as such, both the first coupler MC10 and the second coupler FC10 can thus be connected to and disconnected from the couplers of a fluid flow circuit without leaking large amounts of cooling liquid from the circuit and also without introducing large amounts of air into the circuit. In working embodiments of the service tool 60 built to date, "non-spill" (NS series) couplers produced by the Quick Coupling Division of Parker Hannifin Corporation's Fluid Connectors Group, located in Minneapolis, Minn., have been incorporated and successfully utilized. Couplers produced by other manufacturers, though, may alternatively be incorporated and utilized as well.

As shown in FIGS. 5A through 5D, the fluid transfer duct 61 includes an adjustable control valve 58 for opening and closing the fluid transfer duct 61. As best illustrated in FIG. 5C, the adjustable control valve 58 itself includes a valve body 79, a manipulable handle 59, and a spout 86. Provided with such an adjustable control valve 58, the fluid transfer duct 61 can therefore be opened and closed in a controlled manner by manually turning and adjusting the control valve's handle 59. In this way, precise amounts of fluid can ultimately be introduced into and removed from the chamber 80 in the tube 65 via the fluid transfer duct 61.

As illustrated in FIGS. 5A through 5D, the respective proximal ends of the fluid inlet duct 63, the fluid outlet duct 64, and the fluid transfer duct 61 are all mounted on the second end 72 of the tube 65 by means of an end block mount 62. As best shown in FIGS. 5C and 5D, the end block mount 62 includes a fluid inlet port 87, a fluid outlet port 88, a fluid transfer port 89, and a large tubular bore 78 defined therein so as to establish fluid communication between the fluid inlet duct 63, the fluid outlet duct 64, the fluid transfer duct 61, and the tube 65 when properly mounted together. Though the end block mount 62 may be fabricated from other constituent materials, the end block mount 62 is preferably formed from machined aluminum or the like.

In addition to including an adjustable control valve 58, the fluid transfer duct 61 also preferably includes a removable plug 81 at, on, or near its distal end 92. By including such a removable plug 81, the fluid transfer duct 61 facilitates the easy introduction and removal of fluid into and from the chamber 80 within the tube 65. In the particular embodiment depicted in FIGS. 5A through 5D, the adjustable control valve 58 is operatively mounted on the removable plug 81 itself. In alternative embodiments, however, the control valve 58 and the plug 81 may instead be operatively situated separately within the fluid transfer duct 61. In any such embodiment, the removable plug 81 is preferably composed of a translucent or transparent material, such as a clear or see-through plastic. In this way, a serviceman is better able to visually determine both the presence and amount of any one or more fluids (for example, air, liquid, etc.) within the tube 65. Furthermore, in some practicable embodiments, the removable plug 81 may optionally have a threaded hole defined therethrough with a bleeder screw (not shown) adjustably received within the threaded hole. By including such a threaded hole and bleeder screw, the plug 81 facilitates the controlled "bleeding" and evacuation of, for example, any air bubbles trapped within a liquid inside the service tool 60.

To operate the service tool 60 so as to generally add a controlled amount of cooling liquid into the fluid flow circuit 33, a serviceman fastens one end of a fluid transfer hose 57 to the spout 86 of the tool's adjustable control valve 58 as shown in FIG. 5A. Once the hose 57 is fastened to the spout 86, the service tool 60 is generally upended, and cooling liquid 44 is poured from a container 56 into the elevated free end of the hose 57 as shown in FIG. 4A. As the cooling liquid 44 is poured, the manipulable handle 59 of the tool's adjustable control valve 58 is turned left so as to open the tool's fluid transfer duct 61, and the manipulable handle 68 of the plunger 70 is pulled down from the first end 71 of the tool's tube 65 so as to draw the flow of the liquid 44 into the tube's chamber 80 via suction. By pulling the plunger's handle 68 so as to carefully register or align the fore end 69 of the plunger 70 with one of the graduated markings 66 along the length of the tool's tube 65 as desired, a largely precise and controlled amount of cooling liquid 44 is thereby introduced into the tube's chamber 80. With the service tool 60 still upended, the tool 60 is preferably then gently tapped and/or slightly tilted in various directions by the serviceman so that most to all of any air bubbles trapped within the liquid 44 inside the tool's tube 65 rise and flow out of the tool 60 via the tool's fluid transfer duct 61. Once the cooling liquid 44 within the tool's tube 65 appears to be free from air bubbles, the manipulable handle 59 of the tool's adjustable control valve 58 is turned to the right so as to close the tool's fluid transfer duct 61 and thereby seal the liquid 44 within the tool's tube 65. Once the service tool 60 is sealed shut in this manner, the tool 60 is preferably then gently tapped, shaken, and/or tilted about by the serviceman so as to reveal any possible last remaining air bubbles existing within the tool 60. If any last air bubbles are found to exist, the service tool 60 is upended again, the bubbles are sighted through the transparent plug 81, the control valve 58 is slightly re-opened by turning its handle 59 slightly to the left, and the plunger's handle 68 is pushed slightly back into the tube 65 so as to ultimately "burp" and evacuate the bubbles from the tube's chamber 80 via the tool's fluid transfer duct 61. Once the air bubbles are fully evacuated in this manner, the manipulable handle 59 of the tool's adjustable control valve 58 is turned to the right so as to close the tool's fluid transfer duct 61 and thereby seal the cooling liquid 44 within the tool's tube 65. In embodiments wherein the plug 81 includes the previously mentioned threaded hole with bleeder screw received therein, any remaining air bubbles may alternatively be burped or bled and thereby evacuated from the tool's tube 65 by partially unscrewing and then screwing tight the bleeder screw.

Once a controlled amount of cooling liquid 44 has been introduced into the service tool 60 and air bubbles have been evacuated therefrom, both the fluid transfer hose 57 and the container 56 are removed from the tool 60. After the hose 57 and the container 56 are removed, the service tool 60 is temporarily connected within the fluid flow circuit 33 by means of both its first coupler MC10 and second coupler FC10 as shown in FIG. 4B. As soon as the tool's first and second couplers MC10 and FC10 are properly interconnected with mating couplers FC6 and MC11 in the fluid flow circuit 33, the automatic shut-off valves within the couplers MC10, FC6, FC10, and MC11 are automatically opened so that the chamber 80 within the tool's tube 65 is in fluid communication with the fluid flow circuit 33. At about the same time that the service tool 60 is connected within the fluid flow circuit 33, a fluid flow meter 55 may, as an option, be temporarily connected within the circuit 33 as well. Similar to the service tool 60, the fluid flow meter 55 is connected within the fluid flow circuit 33 by means of its first coupler MC9 and second coupler FC9 as shown in FIG. 4B. As soon as the meter's first and second couplers MC9 and FC9 are properly interconnected with mating couplers FC2 and MC2 in the fluid flow circuit 33, the automatic shut-off valves within the couplers MC9, FC2, FC9, and MC2 are automatically opened so that the fluid flow meter 55 too is in fluid communication with the fluid flow circuit 33. After both the service tool 60 and the fluid flow meter 55 are connected within the fluid flow circuit 33 in this manner, the manipulable handle 68 of the tool's plunger 70 is then pushed toward the first end 71 of the tool's tube 65 so that the controlled amount of cooling liquid 44 within the tube's chamber 80 is injected and transferred into the fluid flow circuit 33 via the corresponding pushing force exerted by the plunger's fore end 69. Once the controlled amount of cooling liquid 44 is transferred into the fluid flow circuit 33, the centrifugal pump 34 is temporarily activated so as to briefly circulate the cumulative amount of cooling liquid 44 through the circuit 33. As the cooling liquid 44 is circulated through the fluid flow circuit 33, the serviceman may then observe and read the fluid flow meter 55 to verify that the cooling liquid 44 is being circulated at a proper flow rate so as to ensure that the x-ray tube 32 will be adequately cooled during actual future operation. Once the cooling liquid's flow rate is verified as proper, the centrifugal pump 34 is turned off, and both the service tool 60 and the fluid flow meter 55 are disconnected and removed from the fluid flow circuit 33. After both the service tool 60 and the fluid flow meter 55 are removed, the couplers MC11 and FC6 are reconnected and the couplers MC2 and FC2 are reconnected as well so that the fluid flow circuit 33 stands ready for full and actual operation.

To operate the service tool 60 so as to generally draw and remove a controlled amount of cooling liquid 44 from the fluid flow circuit 33, a serviceman first pushes on the manipulable handle 68 of the tool's plunger 70 so as to move the plunger's fore end 69 to the second end 72 of the tool's tube 65 and thereby empty the tool 60 of any liquid contents. With the plunger's fore end 69 at the tube's second end 72, the service tool 60 is then temporarily connected within the fluid flow circuit 33 by means of both its first coupler MC10 and second coupler FC10 as shown in FIG. 4B. As mentioned previously, as soon as the tool's first and second couplers MC10 and FC10 are properly interconnected with mating couplers FC6 and MC11 in the fluid flow circuit 33, the automatic shut-off valves within the couplers MC10, FC6, FC10, and MC11 are automatically opened so that the chamber 80 within the tool's tube 65 is in fluid communication with the fluid flow circuit 33. After the service tool 60 is connected within the fluid flow circuit 33 in this manner, the manipulable handle 68 of the tool's plunger 70 is then pulled from the first end 71 of the tool's tube 65 so that a controlled amount of cooling liquid 44 is drawn from the circuit 33 and into the tube's chamber 80 via suction. By pulling the plunger's handle 68 so as to carefully register or align the fore end 69 of the plunger 70 with one of the graduated markings 66 along the length of the tool's tube 65 as desired, a largely precise and controlled amount of cooling liquid 44 is thereby introduced and retained in the tube's chamber 80. Once the controlled amount of cooling liquid 44 is transferred into the tool's tube 65 in this manner, the plunger's position within the tube 65 is held in place, and the service tool 60 is both disconnected and removed from the fluid flow circuit 33.

After the service tool 60 is removed, the couplers MC11 and FC6 are reconnected so that the fluid flow circuit 33 generally stands ready for operation. As an option, the fluid flow meter 55 may also be temporarily connected within the fluid flow circuit 33 and the centrifugal pump 34 may also be briefly activated to thereby check the cooling liquid's flow rate through the circuit 33.

To operate the service tool 60 so as to particularly add a controlled amount of cooling liquid 44 into the fluid flow circuit 33 and thereby properly restore the cumulative amount of liquid 44 in the circuit 33 back up to compensation level, a serviceman first transfers the liquid 44 from the container 56 and into the tool 60 so that the tool's tube 65 is generally filled with the liquid 44. After the service tool 60 is filled, the tool 60 is temporarily connected within the fluid flow circuit 33. Once the service tool 60 is properly connected within the fluid flow circuit 33, the manipulable handle 68 of the tool's plunger 70 is carefully pushed in so as to begin slowly transferring and injecting some to all of the tool's liquid contents into the fluid flow circuit 33. In general, the serviceman continues to inject cooling liquid 44 into the fluid flow circuit 33 in this careful manner until the accumulator's bladder 41, as watchfully observed by the serviceman, is filled with the liquid 44 and fully expanded to a predetermined safe limit of expansion. Once the accumulator's bladder 41 is observed to be filled to its predetermined safe limit of expansion, the serviceman then operates the service tool 60 (i.e., carefully pulls back on the plunger's handle 68) so as to draw and remove a predetermined amount of cooling liquid 44 from the fluid flow circuit 33 so that the accumulator's bladder 41 is rendered minimally taut and is no longer filled and fully expanded with liquid 44. This predetermined amount of cooling liquid 44 which is removed from the fluid flow circuit 33 so that the accumulator's bladder 41 is no longer expanded is conventionally referred to as the circuit's "compensation value" amount. In general, the characteristic "compensation value" associated with a given fluid flow circuit is largely dependent on the circuit's physical characteristics for successfully accommodating and retaining various volumes of fluid. Upon removing this compensation value amount of cooling liquid 44 from the fluid flow circuit 33, the amount of cooling liquid 44 within the circuit 33 is thereby properly restored to compensation level. Once the amount of cooling liquid 44 within the fluid flow circuit 33 is restored to compensation level in this manner, the service tool 60 is disconnected and removed from the circuit 33. After the service tool 60 is removed, the couplers MC11 and FC6 are reconnected so that the fluid flow circuit 33 generally stands ready for operation. As an option, the fluid flow meter 55 may also be temporarily connected within the fluid flow circuit 33 and the centrifugal pump 34 may also be briefly activated to thereby check the cooling liquid's flow rate through the circuit 33.

In general, for restoring the cumulative amount of cooling liquid 44 within the fluid flow circuit 33 back up to compensation level, the fillable volume within the tube 65 of the service tool 60 is preferably greater than the characteristic compensation value of the circuit 33. Most preferably, the fillable volume within the tube 65 of the service tool 60 is at least three times (3 x's) greater than the characteristic compensation value of the fluid flow circuit 33. For example, if the fluid flow circuit 33 has a compensation value of 10 cubic inches, then the tube 65 of the service tool 60 should preferably have a chamber 80 that is sized to retain at least about 30 to 40 cubic inches of liquid. In this way, the potential inconvenience of having to fill the service tool 60 and inject the tool's liquid contents into the fluid flow circuit 33 two or more separate times (i.e., more than one time) before successfully restoring compensation level in the circuit 33 is largely eliminated. Also in this way, using the service tool 60 to measure significant amounts of cooling liquid 44 with a high level of precision is better facilitated.

As is apparent from the detailed description hereinabove, there are numerous advantages in utilizing the service tool 60 instead of utilizing the prior art service tool 50. First, since the service tool 60 includes a fluid-retaining tube 65 that is substantially closed and generally not open to ambient air, the potential for inadvertent cooling liquid spills is greatly reduced when utilizing the tool 60. Second, since the service tool 60 includes (i) a fluid-retaining tube 65 that is substantially closed, (ii) an adjustable control valve 58 that is utile for "burping" trapped air from the tube 65, and also (iii) an optional bleeder screw for further burping or "bleeding" trapped air from the tube 65, the potential for inadvertently introducing significant amounts of air into the fluid flow circuit 33 is also greatly reduced when utilizing the tool 60. Third, the service tool 60 is utile for both injecting and drawing controlled amounts of cooling liquid 44 into and from the fluid flow circuit 33, whereas the prior art service tool 50 is only utile for introducing the liquid 44 into the circuit 33. Fourth, the service tool 60 may optionally remain connected within the fluid flow circuit 33 even when both the centrifugal pump 34 and the fluid flow meter 55 are connected and operating within the circuit 33. The prior art service tool 50, in contrast, generally cannot remain connected within the fluid flow circuit 33 when both the centrifugal pump 34 and the fluid flow meter 55 are connected and operating within the circuit 33. Fifth, since the service tool 60 includes a fluid-retaining tube 65 that is substantially closed and generally not open to ambient air, the service tool 60, after being filled, can generally be tilted in various orientations when injecting cooling liquid 44 into the fluid flow circuit 33. As a result, the service tool 60 can generally be utilized to inject cooling liquid 44 into the fluid flow circuit 33 even when the circuit 33 along with the x-ray tube 32 is rotated on the CT imaging system's gantry 27 to various different positions. For example, if the gantry 27 is rotated and stopped such that the fluid flow circuit 33 along with the x-ray tube 32 is situated at either a 3 o'clock position or a 9 o'clock position instead of at the 12 o'clock position 31 as shown in FIG. 1, the service tool 60 can be tilted and oriented as necessary and thus still be successfully utilized to inject cooling liquid 44 into the circuit 33. Such flexibility during use is ideal, for a serviceman can now use the service tool 60 to inject cooling liquid 44 into the fluid flow circuit 33 when the gantry 27 is rotated and stopped with the circuit 33 situated waist high to the serviceman. Hence, using the service tool 60 to inject cooling liquid 44 into the fluid flow circuit 33 is oftentimes safer than using the prior art service tool 50, for use of the tool 60 obviates a serviceman's occasional need to use a stepladder when injecting liquid 44 into the circuit 33. Lastly, though the service tool 60 is utile for transferring cooling liquid 44 into and from the fluid flow circuit 33 of an x-ray tube cooling system, the service tool 60 may also be easily adapted as necessary and used to service various other types of fluid flow circuits including, for example, various hydraulic systems and the like.

In addition to sometimes losing cooling liquid 44 when servicing one or more of the interconnected components within the fluid flow circuit 33 as discussed earlier hereinabove, sometimes a significant amount of air is inadvertently introduced into the circuit 33 as well. In particular, though the circuit's couplers are typically equipped with automatic shut-off valves, air is nevertheless often ingested via one or more of these couplers as they are disconnected and re-connected during service. If such ingestion of air into the fluid flow circuit 33 is not properly corrected, certain consequences may occur. For example, with the introduction of air into the fluid flow circuit 33, hot pockets of air are apt to develop and be circulated through the circuit 33 during operation, thereby reducing the circuit's overall cooling capability. As a result, highly localized heating and burnout of the x-ray tube 32 as well as nearby electrical components may occur. In addition, artifacts may begin to appear in CT scanner images, thereby reducing scanner image resolution and quality. Furthermore, with air pockets circulating through the fluid flow circuit 33, the centrifugal pump 34 is likely to begin "choking" and operating less efficiently, and may even incur damage due to cavitation.

To prevent such potential consequences, various different methods have heretofore been proposed for preventing the inadvertent ingestion of air and/or removing air that has already been ingested into a fluid flow circuit. Such methods proposed to date, however, typically involve numerous steps and are characteristically labor intensive. Consequently, the methods are often rather time-consuming and highly inefficient overall. In addition, since fluid spills when implementing such methods are not uncommon, the methods are frequently quite messy as well. Furthermore, though the above-discussed service tool 60 is utile for injecting and drawing controlled amounts of cooling liquid 44 into and from the fluid flow circuit 33 with minimal spillage and without introducing significant amounts of air into the circuit 33, the tool 60 is generally not practical for removing any air or gas bubbles that may already be present in the circuit 33. In light of such, there is now a clear and present need in the art for a new service tool that is utile for both (i) transferring controlled amounts of liquid into and from a fluid flow circuit with minimal spillage and without introducing significant amounts of air into the circuit and (ii) separating out air or gas bubbles from liquid circulating through the circuit. For some applications, to avoid the inconvenience of ever having to separately connect a fluid flow meter within the fluid flow circuit, it is preferable that such a new service tool also be utile for (iii) monitoring the rate of fluid flow through the circuit.

FIGS. 6 through 19C co-illustrate a newly proposed composite service tool 100 that is generally utile for (i) transferring controlled amounts of fluid into and from a fluid flow circuit, (ii) separating out air or gas bubbles from liquid circulating through the circuit, and (iii) monitoring the rate of fluid flow through the circuit. This composite service tool 100, as depicted, is a second practicable embodiment of the present invention. In its basic form, the composite service tool generally includes a tool for transferring controlled amounts of fluid into and from a fluid flow circuit, a device for removing air or gas bubbles from a liquid, and a fluid flow meter. In order to define at least one fluid flow service path through the composite service tool, the fluid transfer tool, the gas bubble removal device, and the fluid flow meter are integrated together in an interoperable fashion so as to be in fluid communication with each other.

Figure 6:
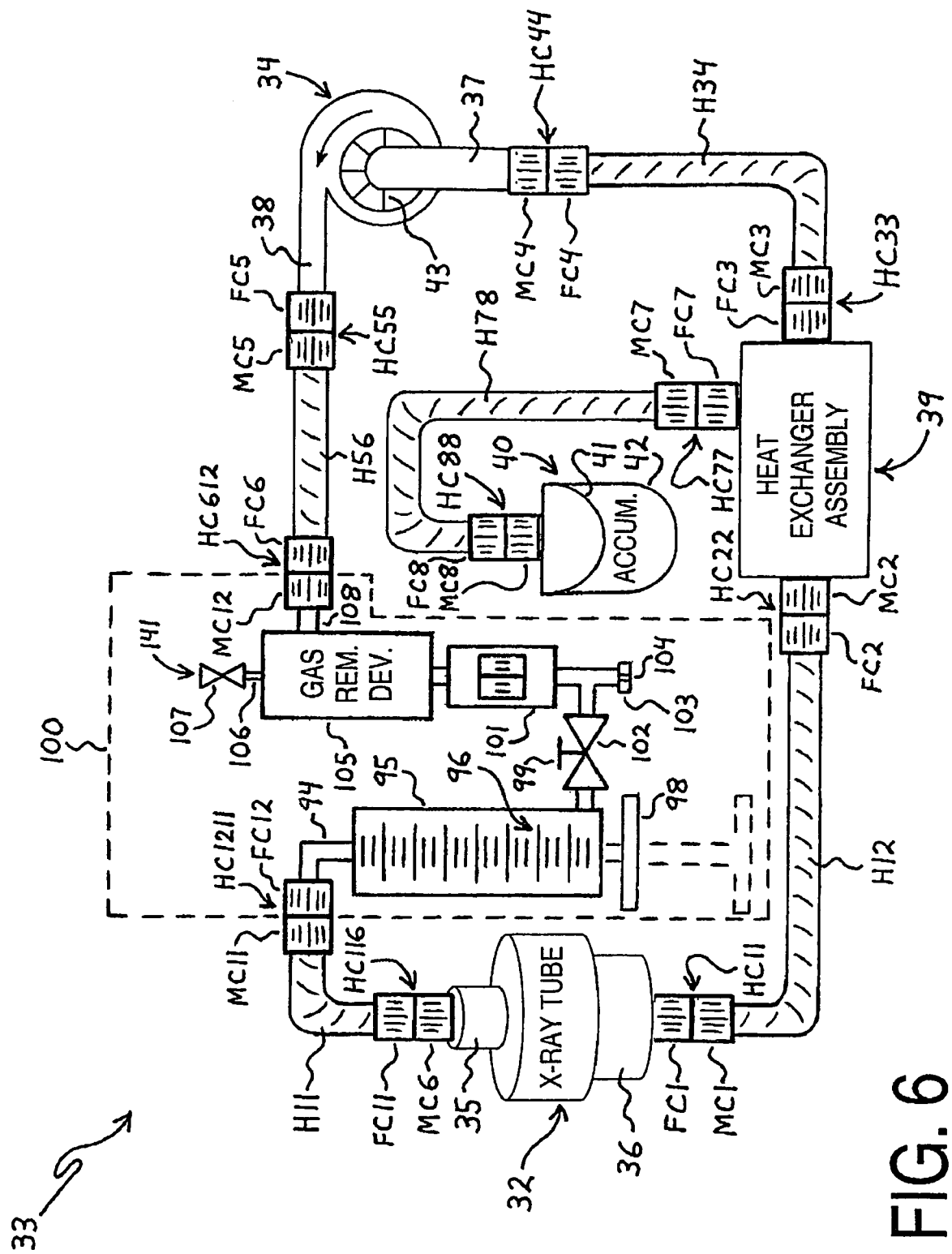
FIG. 6 is an illustration of a composite service tool temporarily connected within the fluid flow circuit of FIG. 2. Connected as such, the composite service tool is operable to transfer a controlled amount of cooling liquid into the fluid flow circuit, separate out gas bubbles from the cooling liquid circulating therein, and monitor the flow rate of the cooling liquid circulating therein. The composite service tool in FIG. 6 is a second practicable embodiment of the invention disclosed herein.
Figure 7A:
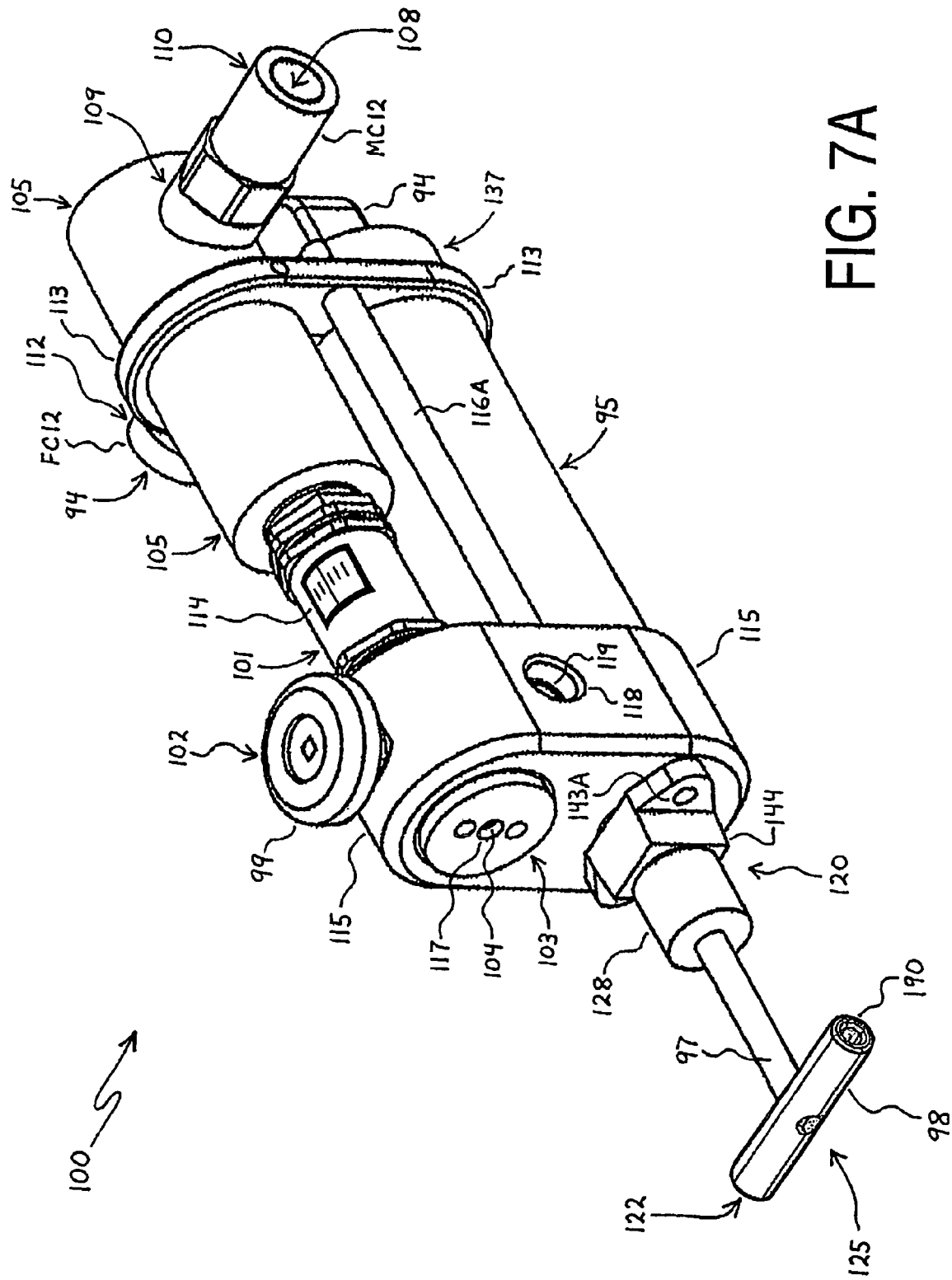
FIG. 7A is a perspective front-to-side view of the composite service tool in FIG. 6.
Figure 7B:
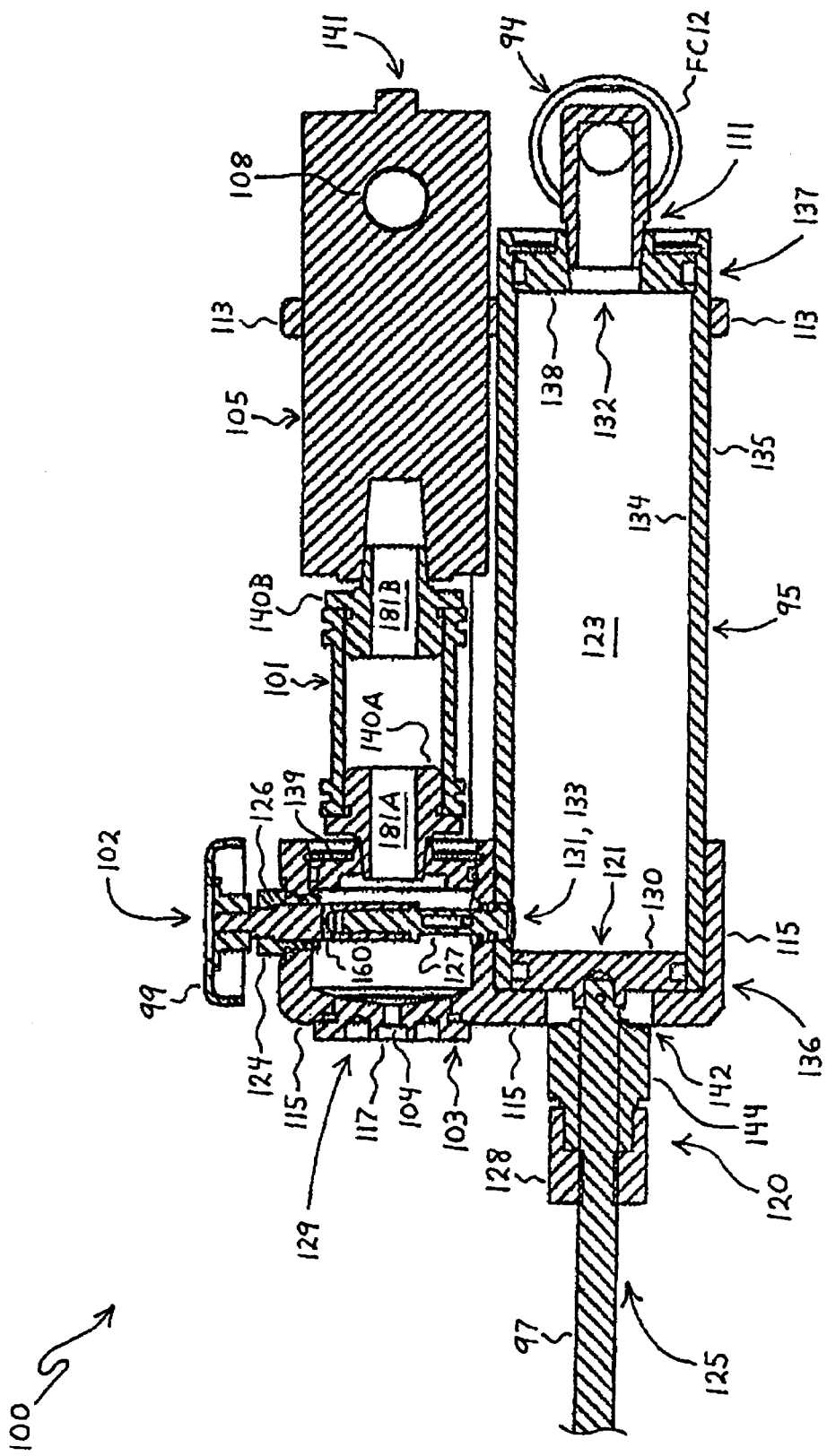
FIG. 7B is a sectional side view of the composite service tool in FIG. 7A.
Figure 7C:
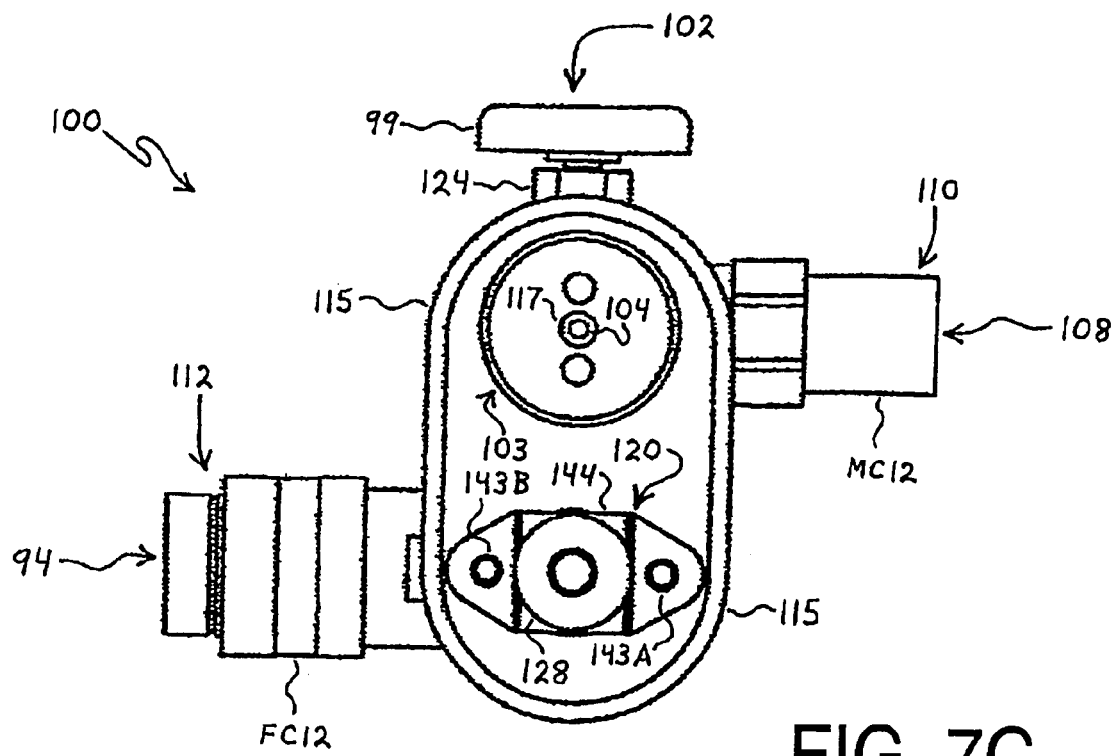
FIG. 7C is a front view of the composite service tool in FIG. 7A.
Figure 7D:
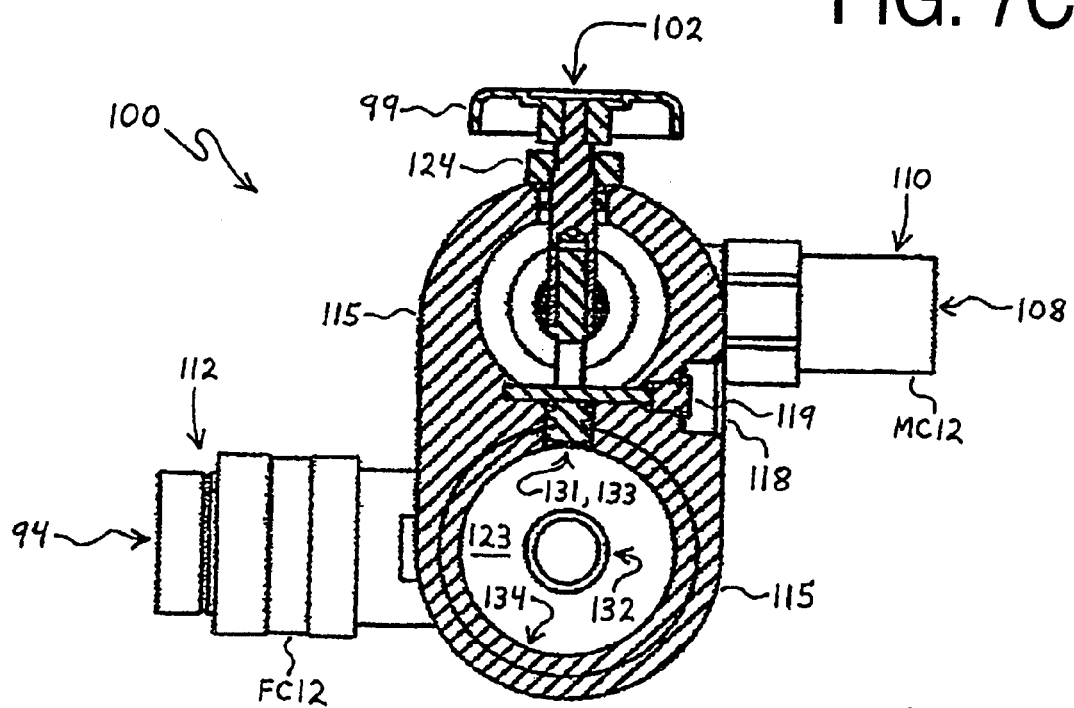
FIG. 7D is a sectional front view of the composite service tool in FIG. 7A.

In the practicable embodiment best illustrated in FIGS. 6 through 7D, the composite service tool 100 itself particularly includes a substantially closed tube 95, an elongate plunger 125, a fluid inlet duct 108, a first coupler MC12, a fluid outlet duct 94, a second coupler FC12, a fluid transfer duct 129, a device 105 for removing gas bubbles from a liquid, and a fluid flow meter 101. The tube 95 comprises translucent material and has a first end 136 and a second end 137, an inner surface 134 and an outer surface 135, a chamber 123 defined therein, a fluid inlet port 131, a fluid outlet port 132 at the second end 137, and graduated markings 96 along the length of the tube 95. The plunger 125 has a fore end 121 that extends inside the tube chamber 123 and toward the second end 137 of the tube 95, and an aft end 122 that extends outside the tube chamber 123 and from the first end 136 of the tube 95. On the fore end 121, the plunger 125 includes a piston-like structure 130 that is adapted for establishing and maintaining close sliding contact and a tight seal between the periphery of the piston-like structure 130 and the inner surface 134 of the tube 95 along the length of the tube 95. On the aft end 122, the plunger 125 includes a manipulable structure 98 that is adapted for adjusting the position of the piston-like structure 130 within the chamber 123 of the tube 95. Each of the fluid inlet duct 108, the fluid outlet duct 94, and the fluid transfer duct 129 respectively has both a proximal end and a distal end. For connecting the fluid inlet duct 108 in line with the fluid flow circuit 33, the first coupler MC12 is mounted on the distal end 110 of the fluid inlet duct 108 and includes an automatic shut-off valve. For connecting the fluid outlet duct 94 in line with the fluid flow circuit 33, the second coupler FC12 is mounted on the distal end 112 of the fluid outlet duct 94 and includes an automatic shut-off valve. Regarding the fluid transfer duct 129, the proximal end of the fluid transfer duct 129 is mounted on the tube 95 so as to be in fluid communication with the chamber 123 inside the tube 95, and the distal end of the fluid transfer duct 129 is oriented so as to extend away from the tube 95. To control amounts of fluid introduced into and removed from the chamber 123 in the tube 95, the fluid transfer duct 129 includes an adjustable control valve 102 for opening and closing the fluid transfer duct 129. Furthermore, in order to define at least one fluid flow service path through the composite service tool 100, the tube 95, the gas bubble removal device 105, and the fluid flow meter 101 are integrated together and connected between the proximal end 109 of the fluid inlet duct 108 and the proximal end 111 of the fluid outlet duct 94 in an interoperable fashion so as to be in fluid communication with each other.

In FIGS. 6 through 7B, the gas bubble removal device 105 included within the composite service tool 100 may generally be any known conventional device that can be connected in line within a fluid flow circuit and that can also remove (i.e., discharge) any air or gas bubbles from a liquid that is circulated through both the circuit and the device. Although other known bubble-removal methods and devices may be utilized, experimentation to date has verified that the bubble-removal methods and devices disclosed in U.S. Pat. No. 5,240,477, issued to J. Yamaga and R. Suzuki on Aug. 31, 1993, and incorporated herein by reference, are generally suitable for implementation and incorporation within the composite service tool 100. More particularly, in actual working embodiments of the composite service tool 100 built to date, a bubble-removal device known as the Bubb-less Eliminator®, produced by Opus Systems Incorporated of Tokyo, Japan, has been incorporated and successfully utilized. Bubble-removal devices produced by other manufacturers, though, may alternatively be incorporated and utilized in the composite service tool 100 as well.

Also in FIGS. 6 through 7B, the fluid flow meter 101 included within the composite service tool 100 may generally be any known conventional meter that can be connected in line within a fluid flow circuit and that can also sense and indicate the fluid flow rate of a liquid that is circulated through both the circuit and the meter. Although other known fluid-flow sensing and indicating meters may be utilized, experimentation to date has verified that the fluid-flow sensing and indicating meters disclosed in U.S. Pat. No. 4,393,723, issued to G. Brand on Jul. 19, 1983, and incorporated herein by reference, are generally suitable for implementation and incorporation within the composite service tool 100. More particularly, in actual working embodiments of the composite service tool 100 built to date, a helical torque type fluid flow meter known as the Visi-Rate™ flow meter, produced by Lake Monitors Incorporated of Milwaukee, Wis., has been incorporated and successfully utilized. Fluid flow meters produced by other manufacturers, though, may alternatively be incorporated and utilized in the composite service tool 100 as well.

Figures 8A, 8B, 8C:
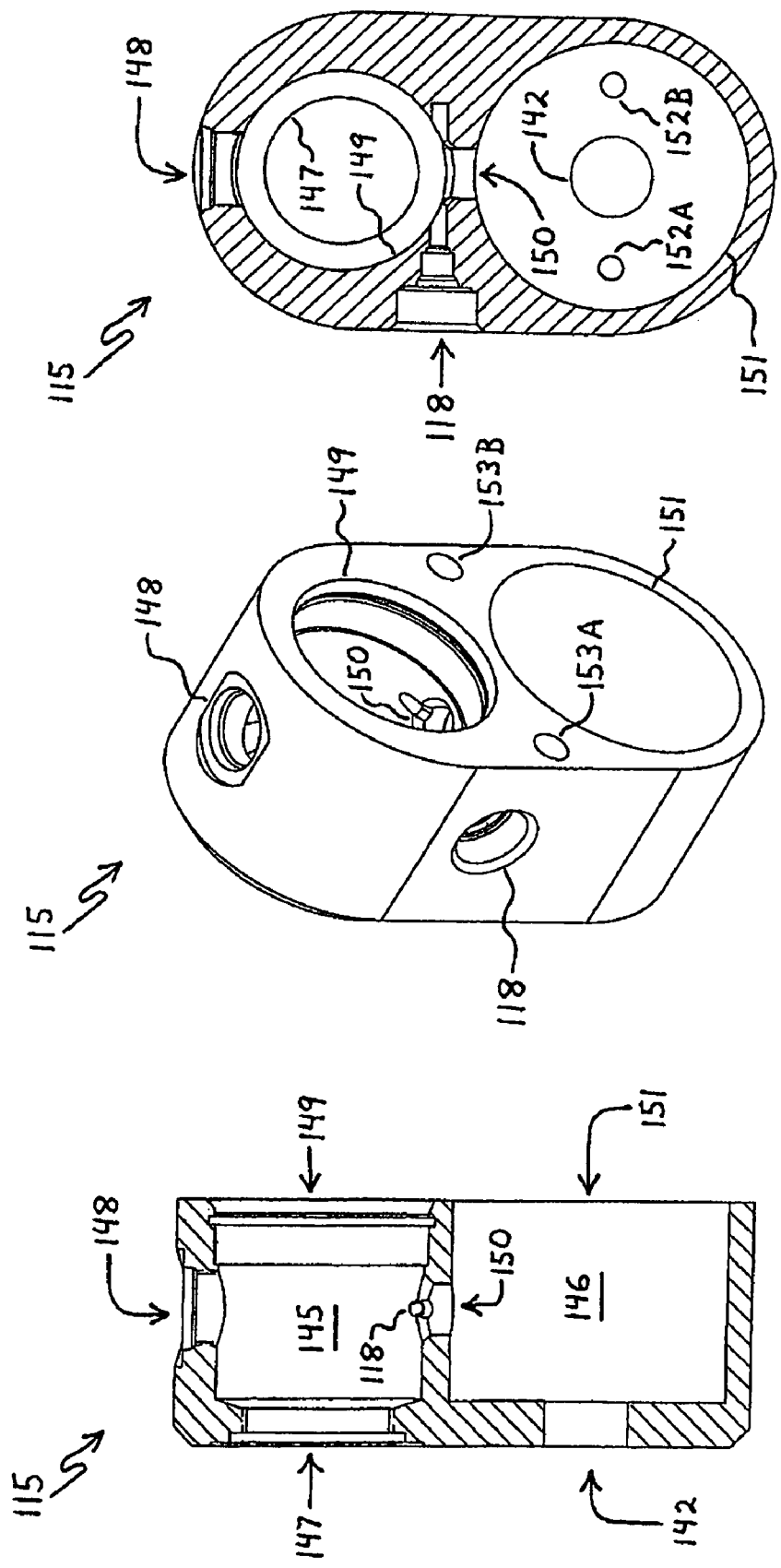
FIG. 8A is a sectional side view highlighting the machined end block mount of the composite service tool in FIGS. 7A and 7B.
FIG. 8B is a perspective side-to-rear view of the machined end block mount in FIG. 8A.
FIG. 8C is a sectional rear view of the machined end block mount in FIG. 8A.

FIGS. 8A through 8C show various sectional and perspective views of an end block mount 115 that is incorporated within the composite service tool 100 as best shown in FIGS. 7A through 7D. In general, the end block mount 115 serves as the primary means by which many of the tool's various constituent parts are mounted on, or held together with, the tube 95. Though the end block mount 115 itself may be fabricated from other constituent materials, the end block mount 115 is preferably formed from machined aluminum or the like.

As illustrated in FIGS. 8A through 8C, the end block mount 115 includes various holes/bores 118, 142, 147, 148, 149, 150, 151, 152A, 152B, 153A, and 153B defined therein. The bore 151, first of all, is shaped and sized so as to closely receive and hold the first end 136 of the tube 95. The bores 148 and 150, in turn, are shaped and sized so as to closely receive various constituent parts of the adjustable control valve 102. The bore 118, next of all, is sized for closely receiving an insertable dowel pin 119 that serves, in general, to maintain both vertical and lateral sliding alignment of the adjustable control valve's stem 127 within the bore 150. As further shown in FIGS. 8A through 8C, both the bore 147 and the bore 149 particularly include either a lip or a groove defined on or within the end block mount 115. Provided with such, the bore 147 is able to receive a removable plug 103, which can be tightly snapped into the bore 147 and also easily popped out of the bore 147 as desired, and the bore 149 is able to tightly capture a machined end cap 139 associated with the fluid flow meter 101. The hole 142, next of all, is generously sized for permitting back-and-forth movement of the plunger's shaft 97, while the left and right bores 152B and 152A are sized so as to closely receive screws or bolts for mounting a lock-and-release assembly 120 for the plunger 125. The left and right bores 153B and 153A, last of all, are particularly threaded. As such, the left and right bores 153B and 153A are suited for respectively receiving and holding the threaded first ends 171B and 171A of left and right clamping rods 116B and 116A.

Figure 9A:
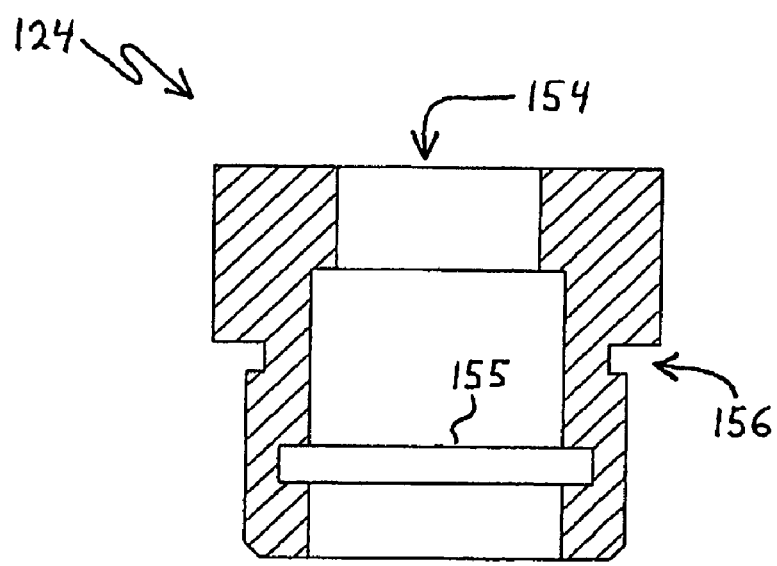
FIG. 9A is a sectional side view highlighting the valve packing nut of the composite service tool in FIG. 7B.
Figure 9B:
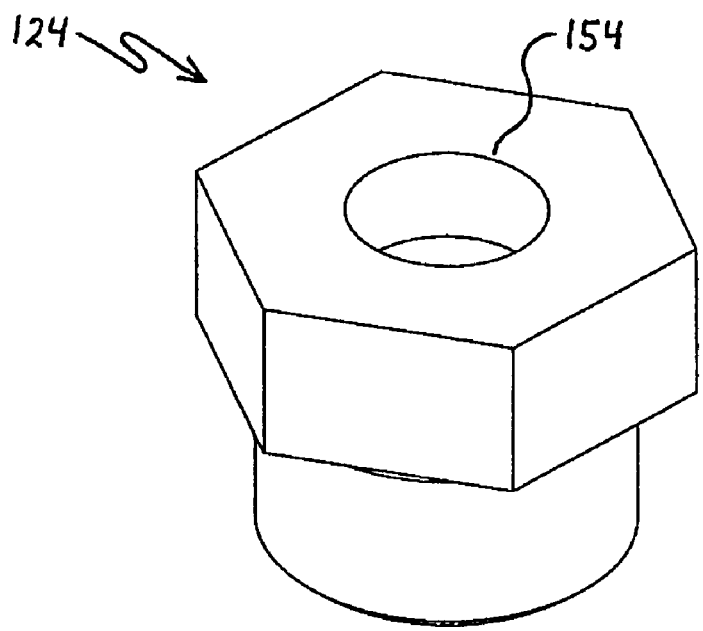
FIG. 9B is a perspective top view of the valve packing nut in FIG. 9A.

FIGS. 9A and 9B show sectional and perspective views of a valve packing nut 124 that is incorporated within the composite service tool 100 as best shown in FIG. 7B. In general, the valve packing nut 124 serves to help orient and retain various constituent parts of the adjustable control valve 102 within the bore 148 defined in the top of the end block mount 115. Though the valve packing nut 124 itself may be fabricated from other constituent materials, the valve packing nut 124 is preferably formed from stainless steel or the like. As illustrated in FIGS. 9A and 9B, the valve packing nut 124 includes an axial bore 154, an inner circular groove 155, and an outer circumferential groove 156. The axial bore 154, first of all, is shaped and sized so as to closely receive the valve body 126 of the adjustable control valve 102 and also permit up-and-down sliding movement of the valve body 126 within the axial bore 154. The inner circular groove 155, in turn, is sized for closely receiving and retaining an o-ring (not shown). The o-ring serves to help establish and maintain a tight seal between the inner surface of the nut's axial bore 154 and the outer surface of the valve body's middle section 158, even when the valve body 126 is slid up and down within the axial bore 154. The outer circumferential groove 156, lastly, is sized for closely receiving and retaining another o-ring (not shown). This second o-ring serves to help establish and maintain a tight and fixed seal between the outer surface of the valve packing nut 124 and the inner surface of the end block mount's bore 148.

FIGS. 10A through 10E show various views of the valve body 126 of the adjustable control valve 102, which is incorporated within the composite service tool 100 as best shown in FIG. 7B. Though the valve body 126 itself may be fabricated from other constituent materials, the valve body 126 is preferably formed from stainless steel or the like. As illustrated in FIGS. 10A through 10E, the valve body 126 includes a top section 157, a middle section 158, and a bottom section 159. The top section 157, first of all, is structurally adapted for affixing a manipulable handle 99 thereon, as best shown in FIG. 7B. The middle section 158, as alluded to previously, is shaped and sized so as to be closely received within the axial bore 154 of the valve packing nut 124 and also permit up and down sliding movement of the valve body 126 within the nut's axial bore 154. The bottom section 159, lastly, includes both a horizontal through hole 160 and an axial bore 161. The axial bore 161 is particularly threaded so as to tightly receive and hold the threaded top section 162 of the adjustable control valve's stem 127.

Figure 11C:
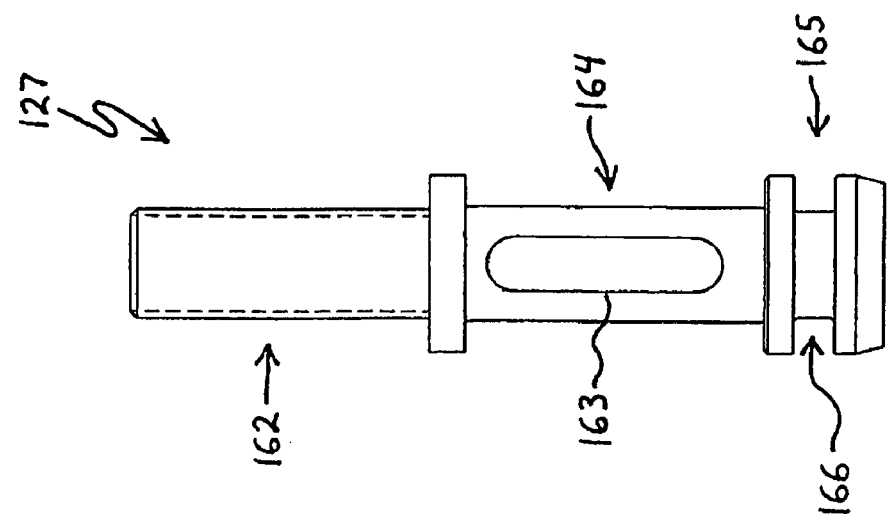
FIG. 11C is a side view of the machined valve stem in FIG. 11A.
Figure 11B:
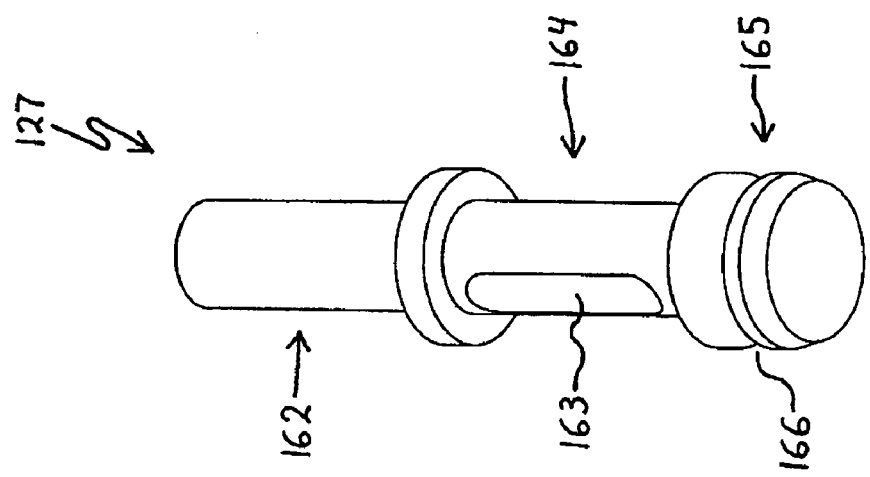
FIG. 11B is a perspective bottom view of the machined valve stem in FIG. 11A.
Figure 11A:
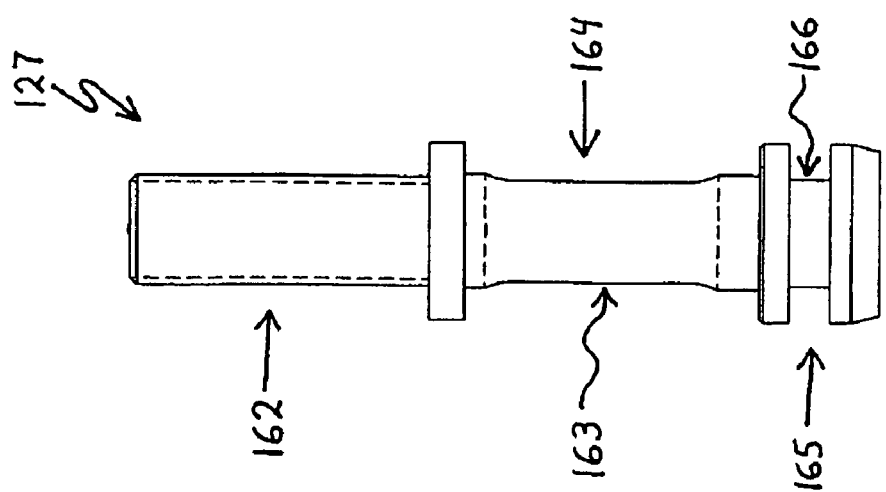
FIG. 11A is a front view highlighting the machined valve stem of the composite service tool in FIG. 7B.

FIGS. 11A through 11C show various views of the valve stem 127 of the adjustable control valve 102, which is incorporated within the composite service tool 100 as best shown in FIG. 7B. Though the valve stem 127 itself may be fabricated from other constituent materials, the valve stem 127 is preferably machined from stainless steel or the like. As illustrated in FIGS. 11A through 11C, the valve stem 127 includes a top section 162, a middle section 164, and a bottom section 165. The top section 162, as alluded to previously, is particularly threaded so as to be tightly received and held within the threaded axial bore 161 of the valve body 126. The middle section 164 of the valve stem 127, in turn, includes a through slot 163. The through slot 163 serves to receive the aforementioned dowel pin 119 in a sliding fashion for thereby maintaining both vertical and lateral sliding alignment of the valve stem 127 during up-and-down manipulation of the adjustable control valve 102. The bottom section 165 of the valve stem 127, lastly, includes a peripheral or outer circumferential groove 166. The outer circumferential groove 166 is sized for closely receiving and retaining an o-ring (not shown). Given such a configuration, whenever the handle 99 of the adjustable control valve 102 is manipulated by a serviceman and particularly pulled upward so that the valve stem 127 is in an up position (as particularly shown in FIG. 7B), the valve stem's o-ring serves to help establish and maintain a tight seal between the outer surface of the valve stem's bottom section 165 and the inner surfaces of both the end block mount's bore 150 and the tube's coinciding fluid inlet port 131 and fluid transfer port 133. In this way, the adjustable control valve 102 can be effectively closed in a tightly sealed fashion.

Figure 12A:
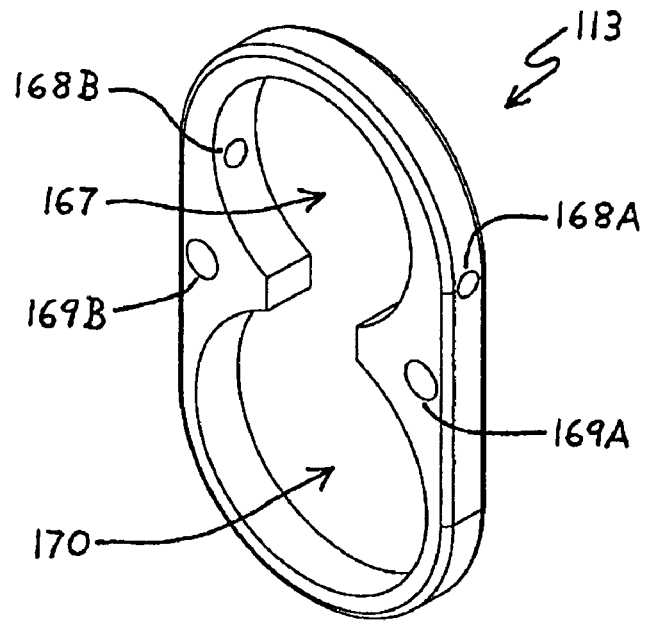
FIG. 12A is a perspective front-to-side view highlighting the machined support plate mount of the composite service tool in FIG. 7A.
Figure 12B:
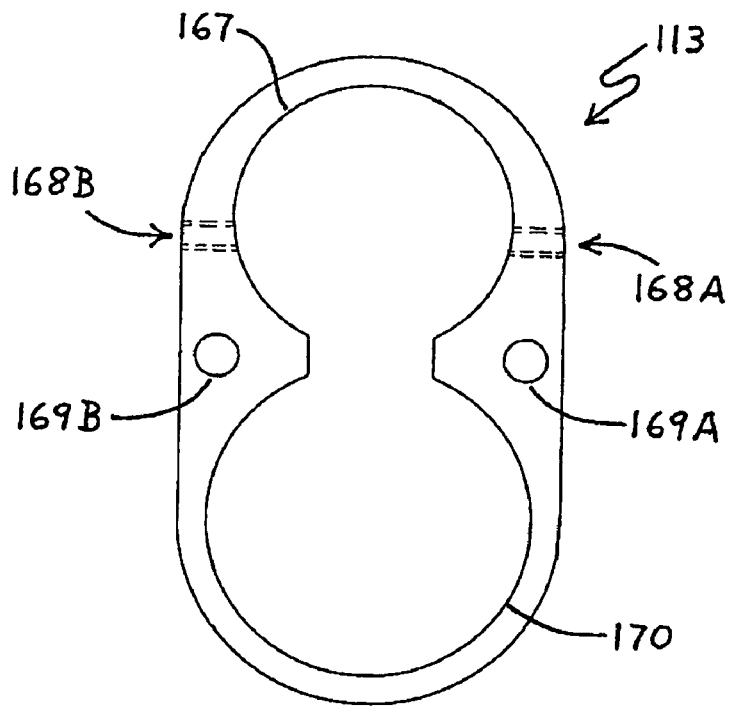
FIG. 12B is a front view of the machined support plate mount in FIG. 12A.

FIGS. 12A and 12B show perspective and frontal views of a support plate mount 113 that is incorporated within the composite service tool 100 as best shown in FIG. 7A. In general, the support plate mount 113, in cooperation with the end block mount 115, serves as means by which many of the tool's various constituent parts are mounted on, or held together with, the tube 95. Though the support plate mount 113 itself may be fabricated from other constituent materials, the support plate mount 113 is preferably machined from aluminum or the like. As illustrated in FIGS. 12A and 12B, the support plate mount 113 includes a large top bore 167, a large bottom bore 170, left and right holes 168B and 168A, and left and right bores 169B and 169A. The large top bore 167, first of all, is shaped and sized for closely receiving and holding the gas bubble removal device 105. The large bottom bore 170, on the other hand, is shaped and sized for closely receiving and holding the tube 95. The left and right holes 168B and 168A, next of all, are sized so as to closely receive screws or bolts for tightly fastening the gas bubble removal device 105 to the support plate mount 113. The left and right bores 169B and 169A, lastly, are particularly threaded. As such, the left and right bores 169B and 169A are suited for respectively receiving and holding the threaded second ends 172B and 172A of the left and right clamping rods 116B and 116A.

Figure 13:
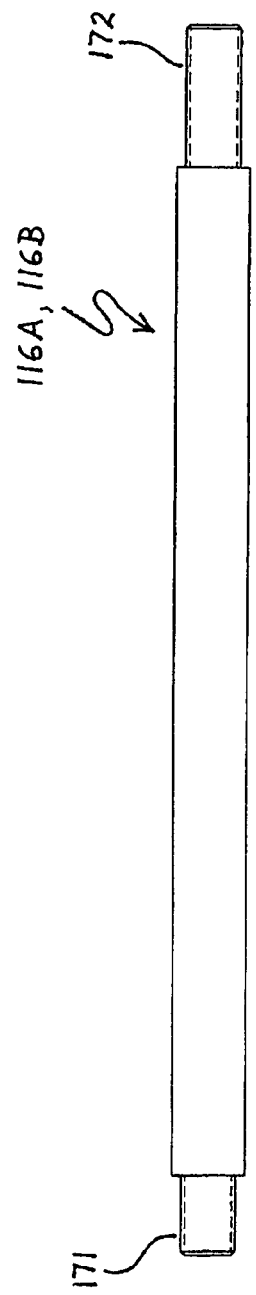
FIG. 13 is a side view highlighting the clamping rod(s) of the composite service tool in FIG. 7A.

FIG. 13 shows a side view of a single clamping rod 116 that is representative of both the left and right clamping rods 116B and 116A that are incorporated within the composite service tool 100 as best shown in FIG. 7A. In general, the left and right clamping rods 116B and 116A, in cooperation with both the support plate mount 113 and the end block mount 115, serve as means by which many of the tool's various constituent parts are held together with the tube 95. Though the left and right clamping rods 116B and 116A may be fabricated from other constituent materials, the rods 116B and 116A are preferably formed from stainless steel or the like. As illustrated in FIG. 13, each clamping rod 116 includes a threaded first end 171 and a threaded second end 172. As alluded to previously, the threaded first ends 171B and 171A of the left and right clamping rods 116B and 116A are sized for being respectively received and held within the threaded left and right bores 153B and 153A of the end block mount 115. The threaded second ends 172B and 172A, on the other hand, are sized for being respectively received and held within the threaded left and right bores 169B and 169A of the support plate mount 113.

Figure 14:
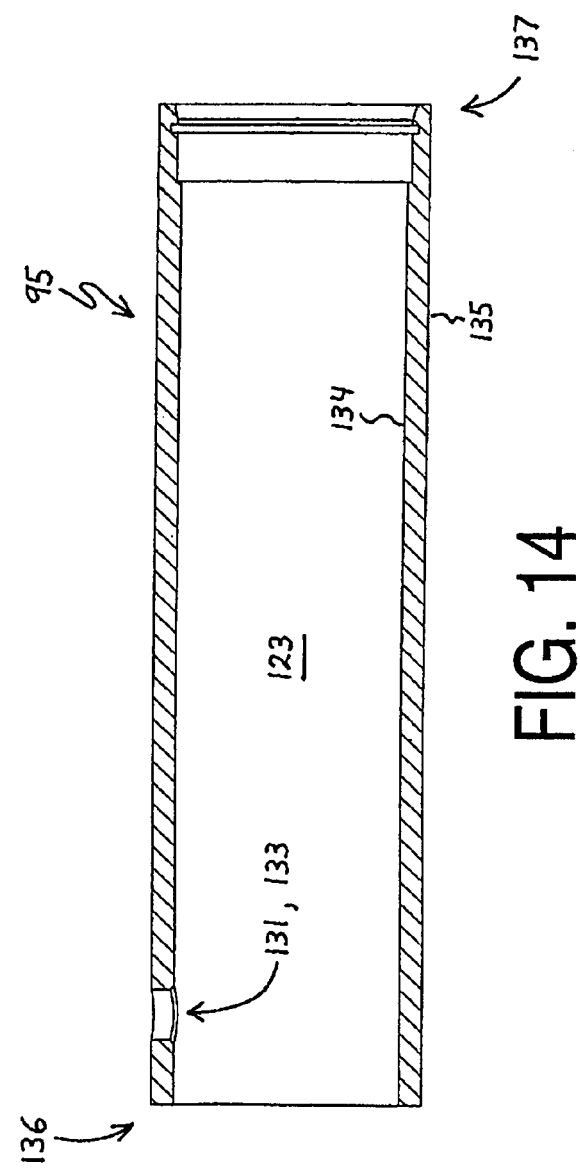
FIG. 14 is a sectional side view highlighting the translucent tube of the composite service tool in FIGS. 7A and 7B.

FIG. 14 shows a sectional side view of the tube 95, which is incorporated within the composite service tool 100 as best shown in FIGS. 7A and 7B. The tube 95 itself preferably has a circular cross section and thus a substantially cylindrical shape overall. In alternative embodiments, however, the tube 95 may instead have a cross section that is, for example, oval, elliptical, polygonal, et cetera. In addition, the tube 95 is preferably formed from a clear, transparent, or translucent material such as shatterproof plastic (polycarbonate). In alternative embodiments, however, the tube 95 may instead be formed from other transparent or translucent materials such as, for example, glass or the like. Composed of such, the tube 95 is characteristically see-through. As a result, a serviceman is generally able to visually determine both the presence and amount of any one or more fluids (for example, air, liquid, etc.) within the tube 95. Furthermore, as shown in FIG. 6, the tube 95 preferably has graduated markings 96 along its length. In having such markings 96, the tube 95 facilitates a serviceman's being able to visually determine amounts of fluid within the tube 95 with more precision.

As co-illustrated in FIGS. 14, 8A, and 7B, the first end 136 of the tube 95 is shaped and sized for being closely received and held within the bore 151 of the end block mount 115. The tube's second end 137, on the other hand, is shaped and sized for being closely received and held within the large bottom bore 170 of the support plate mount 113. As best shown in FIG. 7B, the proximal end 111 of the fluid outlet duct 94 is preferably mounted at or near the second end 137 of the tube 95. Mounted as such, the fluid outlet duct 94 is thereby able to expel the fluid contents of the tube 95 whenever the piston-like structure 130 of the plunger 125 is pushed to the second end 137 of the tube 95.

In FIGS. 14, 7B, and 7A, though both the proximal end 109 of the fluid inlet duct 108 and the proximal end of the fluid transfer duct 129 are shown to be mounted on the tube 95 so as to be in fluid communication with the tube's chamber 123 via a fluid port defined at or near the first end 136 of the tube 95, both the proximal end 109 of the fluid inlet duct 108 and the proximal end of the fluid transfer duct 129 may, in alternative embodiments, be individually mounted and in fluid communication with the tube's chamber 123 via fluid ports defined at various other points along the length of the tube 95, even at or near the second end 137 of the tube 95. Furthermore, though both the fluid inlet duct 108 and the fluid transfer duct 129 are shown to be in fluid communication with the tube's chamber 123 via a fluid inlet port 131 and a fluid transfer port 133 which coincide with each other, the fluid inlet duct 108 and the fluid transfer duct 129 may, in other alternative embodiments, be individually mounted and defined so as to be in fluid communication with the tube's chamber 123 via separate and distinct fluid ports.

Figure 15A:
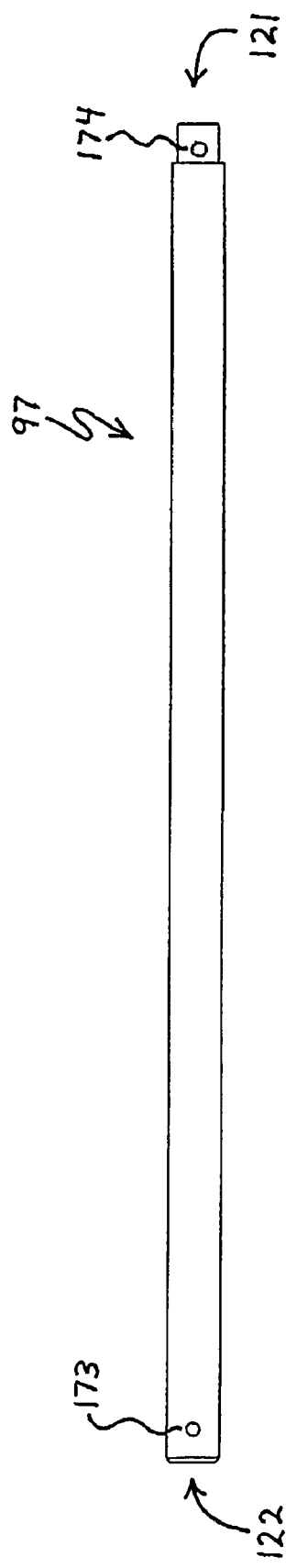
FIG. 15A is a side view highlighting the plunger shaft of the composite service tool in FIGS. 7A and 7B.
Figure 15B:
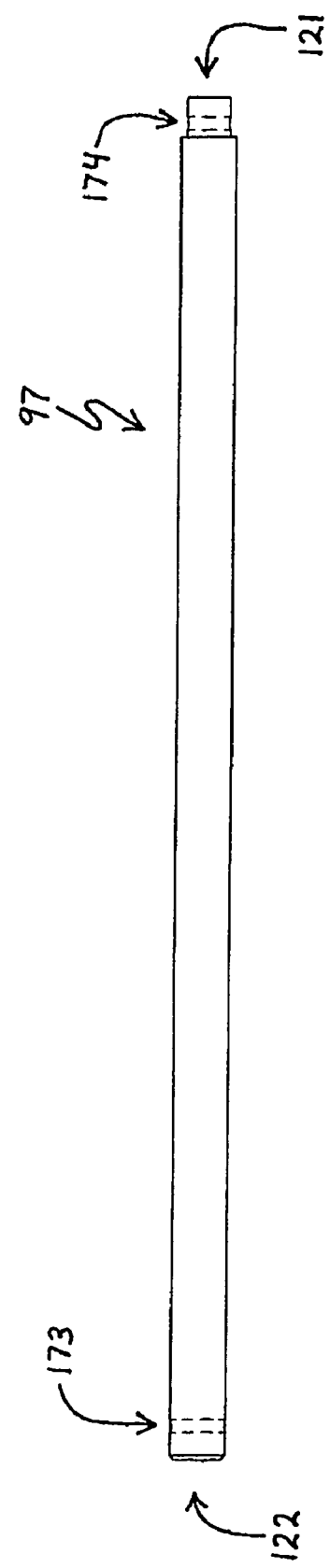
FIG. 15B is a top view of the plunger shaft in FIG. 15A.
Figure 16A:
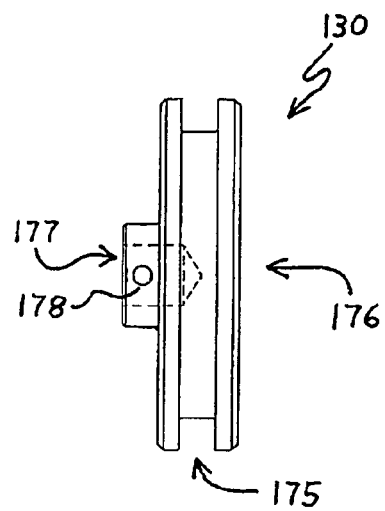
FIG. 16A is a side view highlighting the plunger piston disc of the composite service tool in FIG. 7B.
Figure 16B:
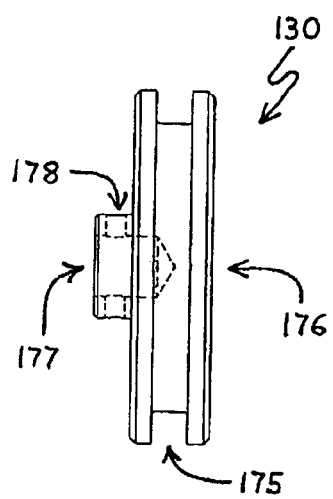
FIG. 16B is a top view of the plunger piston disc in FIG. 16A.
Figure 16C:
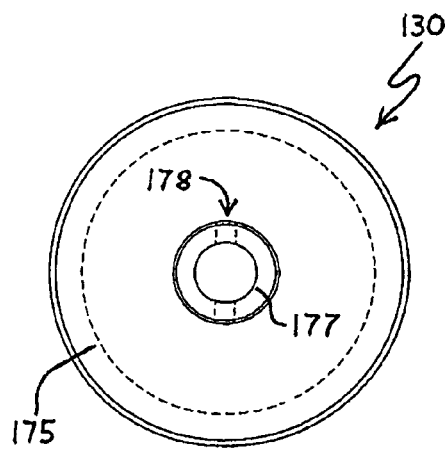
FIG. 16C is a plan view of the plunger piston disc in FIG. 16A.
Figure 16D:
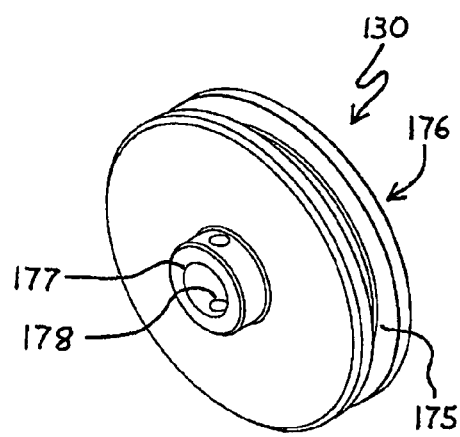
FIG. 16D is a perspective view of the plunger piston disc in FIG. 16A.

FIGS. 15A and 15B respectively show side and top views of the shaft 97 of the plunger 125, which is incorporated within the composite service tool 100 as best shown in FIGS. 7A and 7B. Though the plunger's shaft 97 may be fabricated from other constituent materials, the shaft 97 is preferably formed from steel or the like. As illustrated in FIGS. 15A and 15B, the plunger's shaft 97 includes a through hole 174 defined through its fore end 121 and also a through hole 173 defined through its aft end 122. The through hole 174 is shaped and sized so as to closely receive and hold a bolt or pin for fastening the piston-like structure 130 (for example, a piston disc) onto the shaft's fore end 121. The through hole 173, on the other hand, is shaped and sized so as to closely receive and hold a bolt or pin for fastening the manipulable structure 98 (for example, a handle) onto the shaft's aft end 122.

FIGS. 16A through 16D show various views of the piston disc 130 of the plunger 125, which is incorporated within the composite service tool 100 as best shown in FIG. 7B. Though the piston disc 130 itself may be fabricated from other constituent materials, the piston disc 130 is preferably formed from stainless steel or the like. As illustrated in FIGS. 16A through 16D, the piston disc 130 includes a face 176, an outer circumferential groove 175, an axial bore 177, and a through hole 178. The piston disc's face 176 essentially defines the fore end 121 of the plunger 125 itself, and the disc's outer circumferential groove 175 is sized for closely receiving and retaining an o-ring (not shown). In general, the o-ring serves to establish and maintain both close sliding contact and a tight seal between the periphery of the piston disc 130 and the inner surface 134 of the tube 95 whenever the piston disc 130 is pushed or pulled along the length of the tube 95. Lastly, the piston disc's axial bore 177 is sized and shaped for closely receiving the recessed fore end 121 of the plunger's shaft 97, while the disc's through hole 178 is sized and shaped for being aligned with the shaft's through hole 174 so that a bolt or pin may be commonly received and held to thereby fasten the piston disc 130 onto the shaft 97.

Figure 17C:
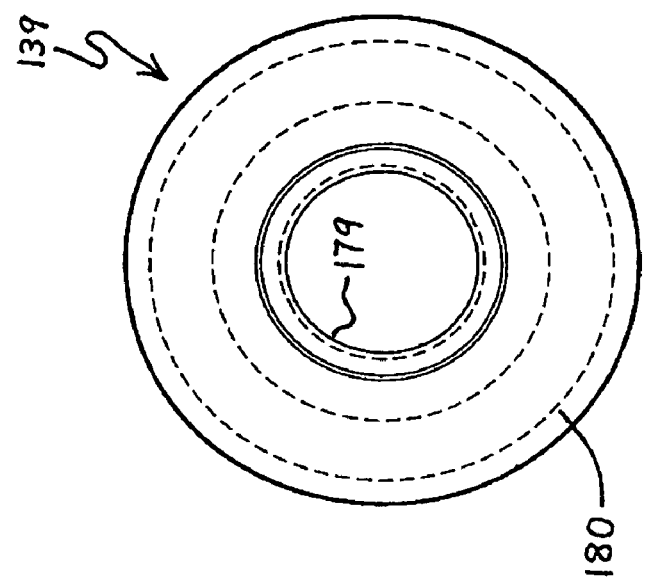
FIG. 17C is a plan view of the machined flow meter end cap in FIG. 17A.
Figure 17B:
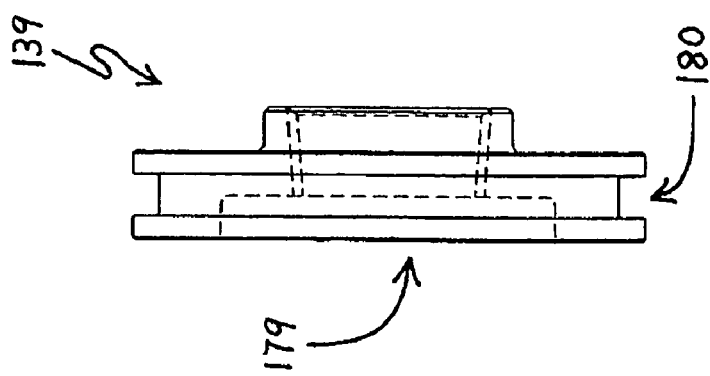
FIG. 17B is a side view of the machined flow meter end cap in FIG. 17A.
Figure 17A:
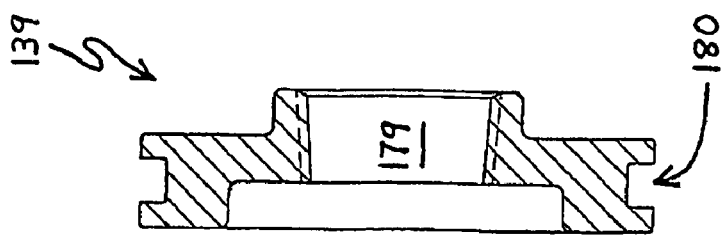
FIG. 17A is a sectional side view highlighting the machined flow meter end cap of the composite service tool in FIG. 7B.

FIGS. 17A through 17C show various views of the flow meter end cap 139, which is incorporated within the composite service tool 100 as best shown in FIG. 7B. In general, the flow meter end cap 139 serves to help mount and capture the downstream end of the fluid flow meter 101 within the bore 149 of the end block mount 115. Though the flow meter end cap 139 itself may be fabricated from other constituent materials, the end cap 139 is preferably machined from stainless steel or the like. As illustrated in FIGS. 17A through 17C, the flow meter end cap 139 includes an axial bore 179 and a circumferential groove 180. The axial bore 179 is sized and threaded for closely receiving and holding the threaded tapering end 185A of a flow meter adapter 140A. The circumferential groove 180 is shaped and sized for closely receiving and retaining an o-ring (not shown). In general, the o-ring serves to ensure that the flow meter end cap 139 is captured within the bore 149 of the end block mount 115 in a tightly sealed manner.

Figure 18C:
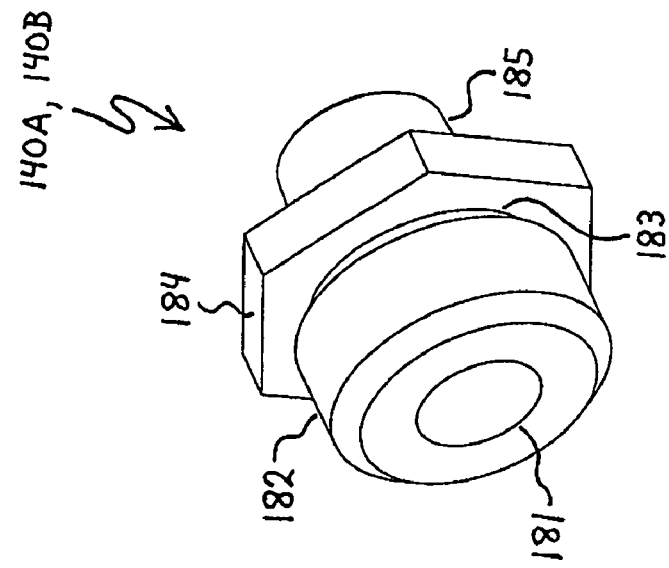
FIG. 18C is a perspective view of the machined flow meter adapter(s) in FIG. 18A.
Figure 18B:
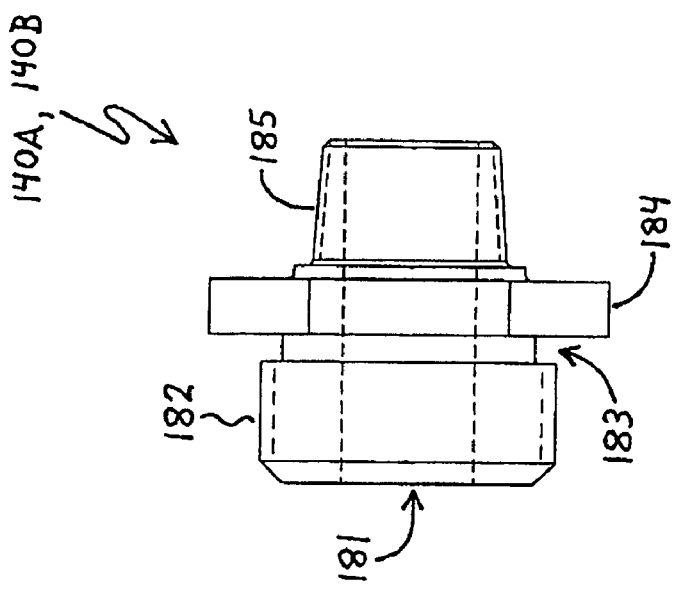
FIG. 18B is a side view of the machined flow meter adapter(s) in FIG. 18A.
Figure 18A:
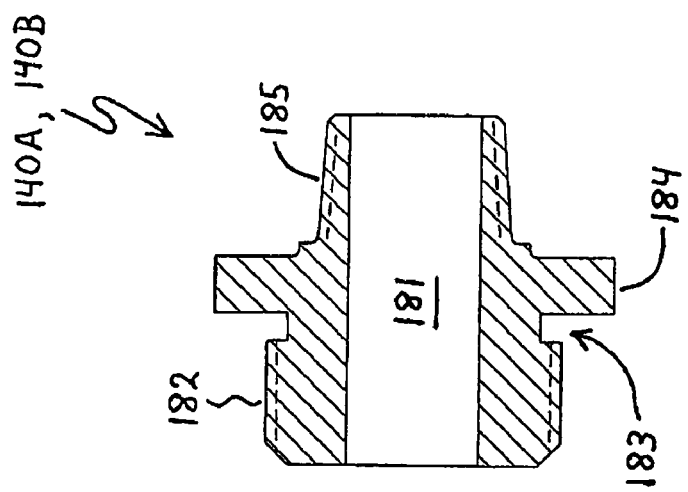
FIG. 18A is a sectional side view highlighting the machined flow meter adapter(s) of the composite service tool in FIG. 7B.

FIGS. 18A through 18C show various views of a single flow meter adapter 140 that is representative of both the upstream and downstream flow meter adapters 140B and 140A that are incorporated within the composite service tool 100 as best shown in FIG. 7B. In general, the upstream and downstream flow meter adapters 140B and 140A serve to help couple and fasten the fluid flow meter 101 between the downstream end of the gas bubble removal device 105 and the bore 149 of the end block mount 115 so as to establish fluid communication therethrough. Though the upstream and downstream flow meter adapters 140B and 140A may be fabricated from other constituent materials, the adapters 140B and 140A are preferably machined from stainless steel or the like. As illustrated in FIGS. 18A through 18C, each flow meter adapter 140 includes an axial bore or conduit 181, a threaded knob end 182, an outer circumferential groove 183, a central flange 184, and a threaded tapering end 185. In general, the axial conduits 181B and 181A respectively defined through the upstream and downstream flow meter adapters 140B and 140A serve to permit the flow of fluid therethrough. With regard to the upstream adapter 140B, the threaded tapering end 185B is sized for being closely received and held within the downstream (i.e., output) end of the gas bubble removal device 105, and the threaded knob end 182B is sized for being closely received and held within the upstream (i.e., input) end of the fluid flow meter 101. With regard to the downstream adapter 140A, the threaded tapering end 185A is sized for being closely received and held within the threaded axial bore 179 of the flow meter end cap 139, and the threaded knob end 182A is sized for being closely received and held within the downstream (i.e., output) end of the fluid flow meter 101. Lastly, the circumferential grooves 183B and 183A respectively defined about the upstream and downstream flow meter adapters 140B and 140A are shaped and sized for closely receiving and retaining o-rings (not shown). In general, each o-ring serves to ensure that the threaded knob end 182 of each flow meter adapter 140 is received and held within an end the fluid flow meter 101 in a tightly sealed manner.

Figure 19C:
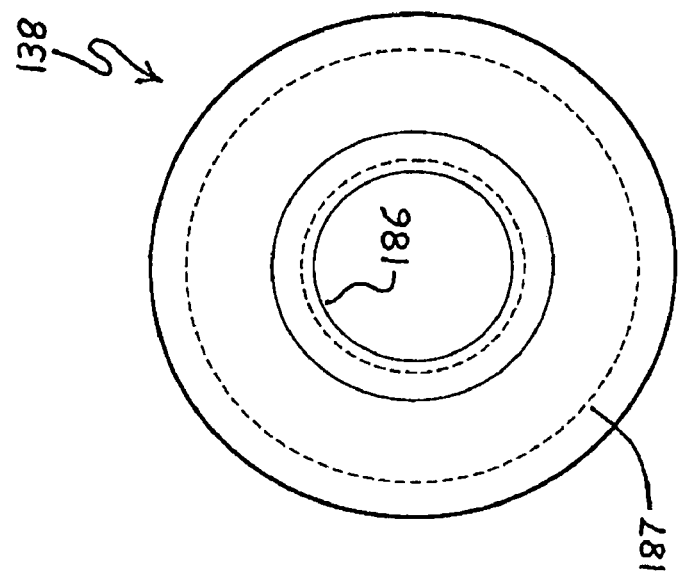
FIG. 19C is a plan view of the machined tube end cap in FIG. 19A.
Figure 19B:
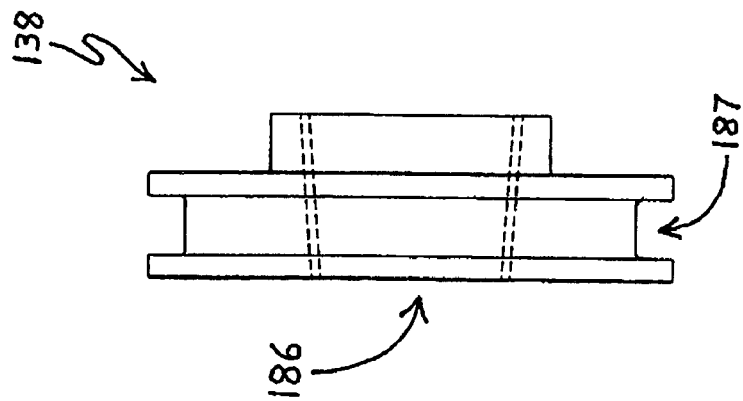
FIG. 19B is a side view of the machined tube end cap in FIG. 19A.
Figure 19A:
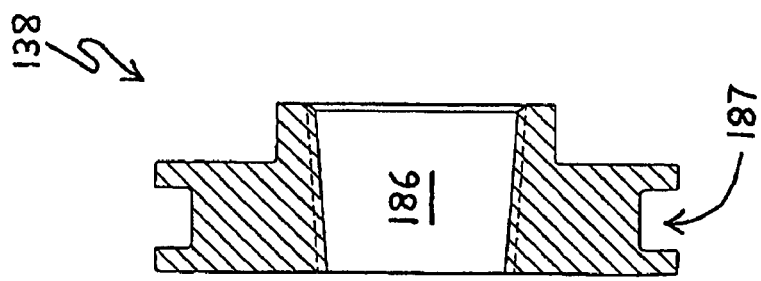
FIG. 19A is a sectional side view highlighting the machined tube end cap of the composite service tool in FIG. 7B.

FIGS. 19A through 19C show various views of the tube end cap 138, which is incorporated within the composite service tool 100 as best shown in FIG. 7B. In general, the tube end cap 138 serves to help mount and capture the proximal end 111 of the fluid outlet duct 94 within the second end 137 of the tube 95. Though the tube end cap 138 itself may be fabricated from other constituent materials, the end cap 138 is preferably machined from stainless steel or the like. As illustrated in FIGS. 19A through 19C, the tube end cap 138 includes an axial bore 186 and a circumferential groove 187. The axial bore 186 is sized and threaded for closely receiving and holding the threaded proximal end 111 of the fluid outlet duct 94. The circumferential groove 187 is shaped and sized for closely receiving and retaining an o-ring (not shown). In general, the o-ring serves to ensure that the tube end cap 138 is captured within the second end 137 of the tube 95 in a tightly sealed manner.

In general, the composite service tool 100 is operated in a manner that is somewhat similar to the manner in which the aforementioned service tool 60 is operated. For example, to operate the composite service tool 100 so as to particularly add a controlled amount of cooling liquid 44 into the fluid flow circuit 33 and thereby properly restore the cumulative amount of liquid 44 in the circuit 33 back up to compensation level, a serviceman first pops the removable plug 103 out of the bore 147 of the end block mount 115 so as to temporarily remove the plug 103 from the end block mount 115. With the plug 103 removed, the serviceman then pushes the handle 99 of the adjustable control valve 102 downward so as to slide the bottom section 165 of the valve stem 127 completely through the bore 150 of the end block mount 115 and into the tube's chamber 123 so that the valve stem 127 is in a down position and the control valve 102 is effectively opened. Once the adjustable control valve 102 is opened, the manipulable handle 98 of the plunger 125 is pulled so that the plunger's piston disc 130 is moved to the first end 136 of the composite service tool's tube 95, and the plunger 125 is then temporarily locked in place with the lock-and-release assembly 120. Once the plunger 125 is locked in place, the composite service tool 100 is upended and cooling liquid 44 from the container 56 is then poured via the hose 57 into the open bore 147 of the upended tool 100 until the tool 100, including both the tool's tube 95 and the end block mount's upper chamber 145, is completely filled with the liquid 44. After the composite service tool 100 is filled with cooling liquid 44, both the container 56 and the hose 57 are removed, and the plug 103 is then snapped back into the bore 147 so that the composite service tool 100 is tightly sealed. With the composite service tool 100 sealed and still generally upended, the tool 100 is preferably then gently tapped and/or slightly tilted in various directions by the serviceman so that most to all of any air bubbles trapped within the liquid 44 inside the tool 100 are forced to rise within the tool 100 and collect at the center of the transparent plug 103. If any air bubbles are sighted by the serviceman through the transparent plug 103, a threaded bleeder screw 104 received within a threaded hole defined in the center of the transparent plug 103 is then slightly turned to the left as necessary so as to bleed and evacuate the air bubbles from the tool 100. Once the cooling liquid 44 within the composite service tool 100 appears to be free from air bubbles, the bleeder screw 104 is then turned back to the right so as to close and seal the tool 100.

Once the composite service tool 100 is both filled with cooling liquid 44 and free from air bubbles, the tool 100 is temporarily connected within the fluid flow circuit 33 as shown in FIG. 6. Once the composite service tool 100 is properly connected within the fluid flow circuit 33, the centrifugal pump 34 is briefly activated so as to circulate all cooling liquid 44 through the circuit 33. As the cooling liquid 44 is circulated through the fluid flow circuit 33, the cooling liquid 44 is also communicated and passed through the fluid inlet duct 108, the gas bubble removal device 105, the fluid flow meter 101, the end block mount 115, the tube 95, and the fluid outlet duct 94 of the composite service tool 100. As the cooling liquid 44 is passed through the gas bubble removal device 105, any air or gas bubbles, whether previously present or newly introduced, in the fluid flow circuit 33 are separated out by the device 105 and discharged via an air/gas vent 141. During this same time, the serviceman may observe and read the composite service tool's fluid flow meter 101 to verify that the cooling liquid 44 is being circulated through the fluid flow circuit 33 at a proper flow rate. Once all air bubbles are discharged from the fluid flow circuit 33 and the cooling liquid's flow rate is verified as proper, the centrifugal pump 34 is turned off.

After the centrifugal pump 34 is turned off, the manipulable handle 99 of the adjustable control valve 102 is pulled up so as to effectively close the control valve 102 and thereby seal shut the composite service tool's tube 95. Once the tube 95 is sealed shut, the lock-and-release assembly 120 is unlocked so as to release the plunger's shaft 97 and thereby permit movement of the plunger 125 by the serviceman. After the plunger 125 is released, the manipulable handle 98 of the tool's plunger 125 is carefully pushed in so as to begin slowly transferring and injecting some to all of the tool tube's liquid contents into the fluid flow circuit 33. In general, the serviceman continues to inject cooling liquid 44 into the fluid flow circuit 33 in this careful manner until the accumulator's bladder 41, as watchfully observed by the serviceman, is filled with the liquid 44 and fully expanded to its predetermined safe limit of expansion. Once the accumulator's bladder 41 is observed to be filled to its predetermined safe limit of expansion, the serviceman then operates the composite service tool 100 (i.e., carefully pulls back on the plunger's handle 98) so as to draw and remove a predetermined compensation value amount of cooling liquid 44 from the fluid flow circuit 33 so that the accumulator's bladder 41 is rendered minimally taut and is no longer filled and fully expanded with liquid 44. Upon removing this compensation value amount of cooling liquid 44 from the fluid flow circuit 33, the amount of cooling liquid 44 within the circuit 33 is thereby properly restored to compensation level. Once the amount of cooling liquid 44 within the fluid flow circuit 33 is restored to compensation level in this manner, the composite service tool 100 is disconnected and removed from the circuit 33. After the composite service tool 100 is removed, the couplers MC11 and FC6 are reconnected so that the fluid flow circuit 33 generally stands ready for operation.

As is apparent from the detailed description hereinabove, there are numerous advantages in utilizing the composite service tool 100 instead of utilizing the prior art service tool 50. In addition to having many of the same aforementioned advantages as the service tool 60 has, the composite service tool 100 also has the advantages of being able to (i) separate out air or gas bubbles from the cooling liquid 44 circulating through the fluid flow circuit 33 and (ii) monitor the rate of fluid flow through the circuit 33 while avoiding the inconvenience of ever having to separately connect the fluid flow meter 101 within the circuit 33.

Parts List

To facilitate a proper understanding of the present invention, a list of parts and features highlighted with alphanumeric designations in FIGS. 1 through 19C is set forth hereinbelow.
20 CT imaging system or scanner
21 patient aperture or opening
22 subject or patient
23 motorized patient table
24 arcuate detector
25 x-ray detector elements
26 6 o'clock position
27 rotatable gantry
28 gantry axis
29 anatomical section or region of interest (ROI)
30 fan-shaped beam of x-rays
31 12 o'clock position
32 x-ray tube (with housing)
33 fluid flow circuit (for an x-ray tube cooling system)
34 centrifugal pump
35 anode end (of x-ray tube)
36 cathode end (of x-ray tube)
37 suction line (inlet)
38 discharge line (outlet)
39 heat exchanger assembly
40 accumulator
41 expandable membrane (a bladder, diaphragm, or bellows)
42 outer housing
43 impeller
44 cooling liquid (for example, oil)
45 bottle or container
46 funnel
47 graduated cylinder
48 graduated markings
49 piping
50 service tool (prior art)
51 backflow prevention valve
52 air jack
53 air hose
54 hand-squeezable inflation bulb
55 fluid flow meter
56 bottle or container
57 fluid transfer hose
58 adjustable control valve
59 manipulable handle
60 service tool
61 fluid transfer duct
62 machined end block mount
63 fluid inlet duct
64 fluid outlet duct
65 translucent tube
66 graduated markings
67 shaft (of plunger)
68 manipulable structure (for example, a handle)
69 fore end (of plunger)
70 elongate plunger
71 first end (of tube)
72 second end (of tube)
73 aft end (of plunger)
74 inner surface (of tube)
75 outer surface (of tube)
76 duct alignment axis
77 tube end cap (with hole)
78 tubular bore (for closely receiving tube)
79 valve body
80 hollow or chamber (within tube)
81 removable plug (preferably transparent or translucent)
82 proximal end (of fluid inlet duct)
83 distal end (of fluid inlet duct)
84 proximal end (of fluid outlet duct)
85 distal end (of fluid outlet duct)
86 valve spout
87 fluid inlet port
88 fluid outlet port
89 fluid transfer port
90 piston-like structure (for example, a piston disc)
91 proximal end (of fluid transfer duct)
92 distal end (of fluid transfer duct)
93 groove (for retaining an o-ring)
94 fluid outlet duct
95 translucent tube
96 graduated markings
97 shaft (of plunger)
98 manipulable structure (for example, a handle)
99 manipulable handle
100 composite service tool
101 fluid flow meter
102 adjustable control valve
103 removable plug (preferably transparent or translucent)
104 bleeder screw
105 gas bubble removal device 106 vent line or conduit
107 vent valve (for bleeding air or gas)
108 fluid inlet duct
109 proximal end (of fluid inlet duct)
110 distal end (of fluid inlet duct)
111 proximal end (of fluid outlet duct)
112 distal end (of fluid outlet duct)
113 machined support plate mount
114 flow rate indicator window
115 machined end block mount
116A right clamping rod
116B left clamping rod
117 threaded hole (for receiving bleeder screw)
118 bore (for receiving dowel pin and hex plug)
119 dowel pin (with hollow hex plug)
120 lock-and-release assembly (for locking/releasing plunger)
121 fore end (of plunger)
122 aft end (of plunger)
123 hollow or chamber (within tube)
124 valve packing nut
125 elongate plunger
126 valve body
127 machined valve stem
128 screwable locking nut
129 fluid transfer duct
130 piston-like structure (for example, a piston disc)
131 fluid inlet port
132 fluid outlet port
133 fluid transfer port
134 inner surface (of tube)
135 outer surface (of tube)
136 first end (of tube)
137 second end (of tube)
138 machined tube end cap
139 machined flow meter end cap
140A machined flow meter adapter (downstream)
140B machined flow meter adapter (upstream)
141 air/gas vent (for discharging air or gas)
142 hole (for receiving shaft of plunger)
143A right bore (for receiving screw or bolt)
143B left bore (for receiving screw or bolt)
144 support piece with guide hole (for receiving plunger shaft)
145 upper hollow or chamber (within end block mount)
146 lower hollow or chamber (within end block mount)
147 bore (for receiving plug)
148 bore (for receiving control valve)
149 bore (for receiving flow meter)
150 bore (for receiving control valve)
151 bore (for receiving tube)
152A right bore (for receiving screw or bolt)
152B left bore (for receiving screw or bolt)
153A right threaded bore (for receiving right clamping rod)
153B left threaded bore (for receiving left clamping rod)
154 axial bore
155 groove (for retaining an o-ring)
156 groove (for retaining an o-ring)
157 top section (of valve body)
158 middle section (of valve body)
159 bottom section (of valve body)
160 through hole
161 threaded axial bore (for receiving valve stem)
162 threaded top section (of valve stem)
163 through slot (for receiving dowel pin)
164 middle section (of valve stem)
165 bottom section (of valve stem)
166 groove (for retaining an o-ring)
167 top bore (for receiving gas bubble removal device)
168A right threaded hole (for receiving screw)
168B left threaded hole (for receiving screw)
169A right threaded bore (for receiving right clamping rod)
169B left threaded bore (for receiving left clamping rod)
170 bottom bore (for receiving tube)
171A threaded first end (of right clamping rod)
171B threaded first end (of left clamping rod)
172A threaded second end (of right clamping rod)
172B threaded second end (of left clamping rod)
173 through hole (for receiving bolt or pin)
174 through hole (for receiving bolt or pin)
175 groove (for retaining an o-ring)
176 face (of piston disc)
177 axial bore (for receiving shaft)
178 through hole (for receiving bolt or pin)
179 threaded axial bore (for receiving flow meter adapter)
180 groove (for retaining an o-ring)
181A axial bore or conduit
181B axial bore or conduit
182A threaded knob end (for receipt within flow meter)
182B threaded knob end (for receipt within flow meter)
183A groove (for retaining an o-ring)
183B groove (for retaining an o-ring)
184A flange
184B flange
185A threaded tapering end (for receipt in flow meter end cap)
185B threaded tapering end (for receipt in gas removal device)
186 threaded axial bore
187 groove (for retaining an o-ring)
188 air release button
189 through hole (for receiving bolt or pin)
190 through hole (for receiving bolt or pin)
FC0 female coupler
FC1 female coupler
FC2 female coupler
FC3 female coupler
FC4 female coupler
FC5 female coupler
FC6 female coupler
FC7 female coupler
FC8 female coupler
FC9 female coupler
FC10 female coupler
FC11 female coupler
FC12 female coupler
H11 hose
H12 hose
H34 hose
H56 hose
H78 hose
HC02 hydraulic coupling
HC11 hydraulic coupling
HC22 hydraulic coupling
HC29 hydraulic coupling
HC33 hydraulic coupling
HC44 hydraulic coupling
HC55 hydraulic coupling
HC66 hydraulic coupling
HC77 hydraulic coupling
HC88 hydraulic coupling
HC92 hydraulic coupling
HC116 hydraulic coupling
HC610 hydraulic coupling HC612 hydraulic coupling
HC1011 hydraulic coupling
HC1211 hydraulic coupling
MC1 male coupler
MC2 male coupler
MC3 male coupler
MC4 male coupler
MC5 male coupler
MC6 male coupler
MC7 male coupler
MC8 male coupler
MC9 male coupler
MC10 male coupler
MC11 male coupler
MC12 male coupler While the present invention has been described in what are presently considered to be its most practical and preferred embodiments or implementations, it is to be understood that the invention is not to be limited to the particular embodiments disclosed hereinabove. On the contrary, the present invention is intended to cover various modifications and equivalent arrangements included within the spirit and scope of the claims appended hereinbelow, which scope is to be accorded the broadest interpretation so as to encompass all such modifications and equivalent structures as are permitted under the law.

What is claimed is:

1. A tool for transferring controlled amounts of fluid into and from a fluid flow circuit, said tool comprising:
    a substantially closed tube having a first end and a second end, an inner surface and an outer surface, and a chamber defined therein;
    an elongate plunger having a fore end extending inside said chamber and toward said second end of said tube, an aft end extending outside said chamber and from said first end of said tube, a piston-like structure on said fore end adapted for establishing and maintaining close sliding contact and a tight seal between the periphery of said piston-like structure and said inner surface of said tube along the length of said tube, and a manipulable structure on said aft end adapted for adjusting the position of said piston-like structure within said chamber of said tube;
    a fluid inlet duct having a proximal end mounted on said tube so as to be in fluid communication with said chamber inside said tube, and a distal end extending from said tube;
    a first coupler mounted on said distal end of said fluid inlet duct for connecting said fluid inlet duct in line with said fluid flow circuit;
    a fluid outlet duct having a proximal end mounted on said second end of said tube so as to be in fluid communication with said chamber inside said tube, and a distal end extending from said tube;
    a second coupler mounted on said distal end of said fluid outlet duct for connecting said fluid outlet duct in line with said fluid flow circuit; and
    a fluid transfer duct having a proximal end mounted on said tube so as to be in fluid communication with said chamber inside said tube, and a distal end extending from said tube;
    wherein said second coupler includes an automatic shut-off valve that automatically opens said fluid outlet duct when connected to said fluid flow circuit and that automatically closes said fluid outlet duct when disconnected from said fluid flow circuit.

2. A tool according to claim 1, wherein said tube has an overall shape that is substantially cylindrical.

3. A tool according to claim 1, wherein said tube comprises translucent material to facilitate visually determining amounts of fluid within said tube.

4. A tool according to claim 3, wherein said tube has graduated markings along the length of said tube to facilitate visually determining amounts of fluid within said tube.

5. A tool according to claim 1, wherein said elongate plunger comprises a shaft that joins said piston-like structure and said manipulable structure together, and said first end of said tube has a hole through which said shaft of said plunger is permitted to slide back and forth.

6. A tool according to claim 1, wherein said manipulable structure comprises a handle.

7. A tool according to claim 1, wherein at least one of said proximal end of said fluid inlet duct and said proximal end of said fluid transfer duct is mounted on said second end of said tube.

8. A tool according to claim 1, wherein at least one of said proximal end of said fluid inlet duct and said proximal end of said fluid transfer duct is mounted proximate said first end of said tube.

9. A tool according to claim 1, wherein said distal end of said fluid inlet duct and said distal end of said fluid outlet duct face in substantially opposite directions to facilitate connecting said tool in line with said fluid flow circuit.

10. A tool according to claim 9, wherein said distal end of said fluid inlet duct and said distal end of said fluid outlet duct are substantially axially aligned with each other to facilitate connecting said tool in line with said fluid flow circuit.

11. A tool according to claim 1, wherein said first coupler includes an automatic shut-off valve that automatically opens said fluid inlet duct when connected to said fluid flow circuit and that automatically closes said fluid inlet duct when disconnected from said fluid flow circuit.

12. A tool according to claim 1, wherein said proximal end of said fluid transfer duct is physically conjoined with one of said proximal end of said fluid inlet duct and said proximal end of said fluid outlet duct.

13. A tool according to claim 1, wherein said fluid transfer duct includes an adjustable control valve for opening and closing said fluid transfer duct to thereby control amounts of fluid introduced into and removed from said chamber in said tube.

14. A tool according to claim 1, wherein said fluid transfer duct includes a removable plug on said distal end to facilitate the introduction and removal of fluid into and from said chamber in said tube.

15. A tool according to claim 14, wherein said removable plug comprises translucent material.

16. A tool according to claim 15, wherein said removable plug has a threaded hole defined therethrough and includes a bleeder screw adjustably received within said threaded hole to facilitate the evacuation of any air trapped within said tool.

17. A service tool for injecting and drawing controlled amounts of liquid into and from a fluid flow circuit with minimal spillage and without introducing significant amounts of air into said fluid flow circuit, said service tool comprising:
    a substantially closed tube comprising translucent material and having a first end and a second end, an inner surface and an outer surface, a chamber defined therein, and graduated markings along the length of said tube;
    an elongate plunger having a fore end extending inside said chamber and toward said second end of said tube, an aft end extending outside said chamber and from said first end of said tube, a piston-like structure on said fore end adapted for establishing and maintaining close sliding contact and a tight seal between the periphery of said piston-like structure and said inner surface of said tube along the length of said tube, and a manipulable structure on said aft end adapted for adjusting the position of said piston-like structure within said chamber of said tube;

a fluid inlet duct having a proximal end mounted on said tube so as to be in fluid communication with said chamber inside said tube, and a distal end extending from said tube;

a first coupler mounted on said distal end of said fluid inlet duct for connecting said fluid inlet duct in line with said fluid flow circuit, said first coupler including an automatic shut-off valve;

a fluid outlet duct having a proximal end mounted on said second end of said tube so as to be in fluid communication with said chamber inside said tube, and a distal end extending from said tube;

a second coupler mounted on said distal end of said fluid outlet duct for connecting said fluid outlet duct in line with said fluid flow circuit, said second coupler including an automatic shut-off valve; and a fluid transfer duct having a proximal end mounted on said tube so as to be in fluid communication with said chamber inside said tube, and a distal end extending from said tube, said fluid transfer duct including an adjustable control valve;

wherein said second coupler includes an automatic shut-off valve that automatically opens said fluid outlet duct when connected to said fluid flow circuit and that automatically closes said fluid outlet duct when disconnected from said fluid flow circuit.

* * * * *

UNITED STATES PATENT AND TRADEMARK OFFICE
CERTIFICATE OF CORRECTION

PATENT NO. : 7,571,750 B2  Page 1 of 1
APPLICATION NO. : 11/161943
DATED : August 11, 2009
INVENTOR(S) : Phouybanhdyt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1019 days.

Signed and Sealed this

Seventh Day of September, 2010

David J. Kappos
*Director of the United States Patent and Trademark Office*